US012715929B2

(12) United States Patent
Adang et al.

(10) Patent No.: US 12,715,929 B2
(45) **Date of Patent: *Aug. 25, 2026**

(54) ANTAGONISTIC ANTI-HUMAN CD40 MONOCLONAL ANTIBODIES

(71) Applicant: DIABETES-FREE, INC., New York, NY (US)

(72) Inventors: Anton Egbert Peter Adang, Utrecht (NL); Mark De Boer, Utrecht (NL)

(73) Assignee: DIABETES-FREE, INC., New York, NY (US)

( * ) Notice: Subject to any disclaimer, the term of this patent is extended or adjusted under 35 U.S.C. 154(b) by 995 days.

This patent is subject to a terminal disclaimer.

(21) Appl. No.: 17/742,702

(22) Filed: May 12, 2022

(65) Prior Publication Data

US 2023/0059094 A1 Feb. 23, 2023

Related U.S. Application Data

(63) Continuation of application No. 16/987,903, filed on Aug. 7, 2020, now Pat. No. 11,396,552, which is a continuation of application No. PCT/NL2019/050086, filed on Feb. 11, 2019.

(30) Foreign Application Priority Data

Feb. 12, 2018 (EP) .................................... 18156288

(51) Int. Cl.
*C07K 16/28* (2006.01)

(52) U.S. Cl.
CPC ...... *C07K 16/2878* (2013.01); *C07K 2317/14* (2013.01); *C07K 2317/565* (2013.01)

(58) Field of Classification Search
CPC ............ C07K 16/2878; C07K 2317/14; C07K 2317/24; C07K 2317/565; C07K 2317/76; C07K 2317/94; A61K 2039/505
See application file for complete search history.

(56) References Cited

U.S. PATENT DOCUMENTS 3,536,809 A 10/1970 Applezweig
3,598,123 A 8/1971 Zaffaroni
3,845,770 A 11/1974 Theeuwes
3,916,899 A 11/1975 Theeuwes
4,008,719 A 2/1977 Theeuwes
4,716,149 A 12/1987 Bonelli
4,723,958 A 2/1988 Pope
4,747,825 A 5/1988 Linkie
4,880,078 A 11/1989 Inoue
4,897,268 A 1/1990 Tice
4,948,592 A 8/1990 Ayer
4,965,251 A 10/1990 Stamatoyannopoulos
5,059,595 A 10/1991 Le Grazie
5,073,543 A 12/1991 Marshall
5,075,109 A 12/1991 Tice
5,120,548 A 6/1992 McClelland
5,223,409 A 6/1993 Ladner
5,290,540 A 3/1994 Prince
5,350,674 A 9/1994 Boenisch
5,354,556 A 10/1994 Sparks
5,399,346 A 3/1995 Anderson
5,403,590 A 4/1995 Forse
5,580,859 A 12/1996 Felgner
5,585,362 A 12/1996 Wilson
5,589,466 A 12/1996 Felgner
5,591,767 A 1/1997 Mohr
5,639,476 A 6/1997 Oshlack
5,674,533 A 10/1997 Santus
5,733,566 A 3/1998 Lewis
5,855,913 A 1/1999 Hanes
5,874,064 A 2/1999 Edwards
5,934,272 A 8/1999 Lloyd
5,985,309 A 11/1999 Edwards
5,985,320 A 11/1999 Edwards
6,019,968 A 2/2000 Platz
6,103,489 A 8/2000 Arakaki
6,207,195 B1 3/2001 Walsh
6,261,569 B1 7/2001 Comis
6,326,193 B1 12/2001 Liu
6,339,069 B1 1/2002 Meers
6,365,185 B1 4/2002 Ritschel
7,741,280 B2 6/2010 Guichard
8,507,448 B2 8/2013 Camussi
8,734,786 B2 5/2014 Miller
8,852,597 B2 10/2014 Noelle
9,289,381 B2 3/2016 Elliott
9,562,088 B2 2/2017 Wagner
9,888,673 B2 2/2018 Hering
(Continued)

FOREIGN PATENT DOCUMENTS

EP 2857033 B1 11/2016
EP 2629797 B1 5/2018
(Continued)

OTHER PUBLICATIONS

Almagro et al., Frontiers in Immunology, 2018, 8: 1751, pp. 1-19.*
Herold et al. (Science Reports, 2017, 7(1):12276, pp. 1-17.*
Murphy et al., Journal of Immunological Methods, 2018, 463: 127-133.*
Adjei, Akwete L. and Julie Garren. "Pulmonary Delivery of Peptide Drugs: Effect of Particle Size on Bioavailability of Leuprolide Acetate in Healthy Male Volunteers." Pharmaceutical Research 7 (2004): 565-569.
Al-Lazikani, B. et al., "Standard conformations for the canonical structures of immunoglobulins" J Mol Biol. 273 (4):927-48 (1997).
Alturaihi et al.: Interaction of CD154 with different receptors and its role in bidirectional signals. Eur J Immunol. Feb. 2015;45(2):592-602.doi: 10.1002/eji.201444941. Epub Dec. 16, 2014.
Anderson, P.J., et al., "Effect of cystic fibrosis on inhaled aerosol boluses" Am Rev Respir Dis. 140(5): 1317-1324 (1989).
(Continued)

*Primary Examiner* — Hong Sang
(74) *Attorney, Agent, or Firm* — Greenberg Traurig, LLP

(57) ABSTRACT

The disclosure concerns antibodies that bind and antagonize CD40. These antibodies are particularly useful to inhibit immune responses and treat auto-immune diseases.

11 Claims, 4 Drawing Sheets

Specification includes a Sequence Listing.

(56) References Cited

U.S. PATENT DOCUMENTS

| | | | | |
|---|---|---|---|---|
| 9,974,855 | B2 | 5/2018 | Yu et al. | |
| 10,561,728 | B2 | 2/2020 | Reimann et al. | |
| 10,772,958 | B2 | 9/2020 | Yu et al. | |
| 10,882,911 | B2 | 1/2021 | Park et al. | |
| 11,396,552 | B2 * | 7/2022 | Adang | C07K 16/2878 |
| 2007/0041971 | A1 | 2/2007 | Wagner | |
| 2008/0305989 | A1 | 12/2008 | Wen | |
| 2008/0311214 | A1 | 12/2008 | Rao | |
| 2008/0318837 | A1 | 12/2008 | Quay | |
| 2011/0229495 | A1 | 9/2011 | Wagner | |
| 2012/0302505 | A1 | 11/2012 | Fetzer | |
| 2017/0355747 | A1 | 12/2017 | Wagner | |
| 2018/0172683 | A1 | 6/2018 | Roberts | |

FOREIGN PATENT DOCUMENTS

| | | | |
|---|---|---|---|
| JP | 2007512243 | A | 5/2007 |
| JP | 2009536522 | A | 10/2009 |
| JP | 2013523130 | A | 6/2013 |
| WO | 9005785 | | 5/1990 |
| WO | 9219244 | | 11/1992 |
| WO | 9732572 | | 9/1997 |
| WO | 9744013 | | 11/1997 |
| WO | 9831346 | | 7/1998 |
| WO | 9966903 | | 12/1999 |
| WO | 0129058 | | 4/2001 |
| WO | 0196584 | | 12/2001 |
| WO | 2005006949 | A2 | 1/2005 |
| WO | 2005044294 | A2 | 5/2005 |
| WO | 2007129895 | A2 | 11/2007 |
| WO | 2009071486 | A1 | 6/2009 |
| WO | 2011123489 | A2 | 10/2011 |
| WO | 2012054584 | A2 | 4/2012 |
| WO | 2016069921 | A1 | 5/2016 |
| WO | 2016196314 | A1 | 12/2016 |
| WO | 2019156565 | A1 | 8/2019 |
| WO | 2020102454 | A1 | 5/2020 |

OTHER PUBLICATIONS

Arano et al., "A novel bifunctional metabolizable linker for the conjugation of antibodies with radionuclides" Bioconjug Chem. 2(2): 71-76 (1991).

Bajorath, J et al., "Identification of residues on CD40 and its ligand which are critical for the receptor-ligand Interaction" Biochemistry. 34(6): 1833-1844 (1995).

Bajorath, J., et al., "Analysis of gp39/CD40 Interactions Using Molecular Models and Site-Directed Mutagenesis" Biochemistry 34(31): 9884-9892 (1995).

Baxendale, J., et al., "Constitutive activation of the CD40 pathway promotes cell transformation and neoplastic growth" Oncogene. 24(53): 7913-7923 (2005).

Bensigner, W., et al., "A phase 1 study of lucatumumab, a fully human anti-CD40 antagonist monoclonal antibody administered intravenously to patients with relapsed or refractory multiple myeloma" Br J Haematol. 159(1): 58-66 (2012).

Biancone, L. et al., "CD40-CD154 interaction in experimental and human disease (review)" Int J Mol Med. Apr. 1999;3(4):343-53. doi: 10.3892/ijmm.3.4.343.

Bonelli, F., et al., "Solid phase synthesis of retro-inverso peptide analogues: Synthesis and biological activity of the partially modified retro-inverso analogue of the bradykinin potentiating peptide BPP9a [gLys6, (RS)-mPhe7, Ala8] BPP9a" Int. J. of Peptide and Protein Research 24(6): 553-556(1984).

Byron, P.R., "Determinants of drug and polypeptide bioavailability from aerosols delivered to the lung" Advanced Drug Delivery Reviews 5(1-2): 107-132 (1990).

Carell, T., et al., "A Novel Procedure for the Synthesis of Libraries Containing Small Organic Molecules" Angew. Chem. Int. Ed. Engl., 33: 2059-2061. https://doi.org/10.1002/anie.199420591 (1994).

Carell, T., et al., "A Solution-Phase Screening Procedure for the Isolation of Active Compounds From a Library of Molecules" Angew Chem Int Ed Engl 33:2061-2064 (1994).

Carstensen , J., "Drug Stability: Principles & Practice" 2d. Ed., Marcel Dekker, NY, NY, (1995), pp. 379-380 ISBN: 0824796357, 9780824796358.

Cencic, R., "Protospacer adjacent motif (PAM)-distal sequences engage CRISPR Cas9 DNA target cleavage", PLoS One. Oct. 2, 2014;9(10):e109213. doi: 10.1371/journal.pone.0109213.

Cho, C. Y., et al., "An Unnatural Biopolymer" Science 261:1303-1305 (1993).

Clark, R., et al. "Long-acting growth hormones produced by conjugation with polyethylene glycol" J Biol Chem. 1996; 271(36):21969-77 doi: 10.1074/jbc.271.36.21969.

Clay, TM, et al., "Assays for monitoring cellular immune responses to active immunotherapy of cancer" May 2001;7 (5):1127-35.

Cleland, J. L., et al., "Formulation and Delivery of Proteins and Peptides: Design and Development Strategies" Chapter 1, pp. 1-19 (1994).

Clothia, C., et al., "Canonical structures for the hypervariable regions of immunoglobulins" J Mol Biol. Aug. 20, 1987;196(4):901-17. doi: 10.1016/0022-2836(87)90412-8.

Cull, S. E., et al., "Screening for Receptor Ligands Using Large Libraries of Peptides Linked to the C Terminus of the Iac Repressor" Proc Natl Acad Sci U S A. Aug. 1990;87(16):6378-82. doi: 10.1073/pnas.87.16.6378.

Dai, W., et al., "Characterization of physiochemical and biological properties of an insulin/lauryl sulfate complex formed by hydrophobic ion pairing" Int J Pharm. 336(1): 58-66 (2007).

Dawson, P. E., et al., "Synthesis of native proteins by chemical ligation" Annu Rev Biochem. 69: 923-960 (2000).

Deambrosis, I., et al., "Inhibition of CD40-CD154 costimulatory pathway by a cyclic peptide targeting CD154" J Mol Med (Berl). 87(2): 181-197 (2009).

Devlin, J. J., et al. "Random peptide libraries: a source of specific protein binding molecules" Science 249 (4967):404-406 (1990).

Dewitt, S.H., et al. "Diversomers": an approach to nonpeptide, nonoligomeric chemical diversity. Proc Natl Acad Sci U S A. Aug. 1, 1993;90(15):6909-13.

Dreborg, S., et al., "Immunotherapy with monomethoxypolyethylene glycol modified allergens" Crit Rev Ther Drug Carrier Syst. 6(4): 315-365 (1990).

Duncan, R., et al., "Soluble synthetic polymers as potential drug carriers" Polymers in Medicine 57: 51-101 (1984).

Erb, E., et al. Recursive deconvolution of combinatorial chemical libraries. PNAS USA 91(24):11422-11426 (1994).

Felici, F., et al., "Selection of antibody ligands from a large library of oligopeptides expressed on a multivalent exposition vector" J Mol Biol 222:301-310 (1991).

Fodor, S. P., et al., "Multiplexed biochemical assays with biological chips" Nature. Aug. 5, 1993;364(6437):555-6.

French, A., et al., "Human induced pluripotent stem cell-derived B lymphocytes express sigM and can be generated via a hemogenic endothelium intermediate" Stem Cells Dev. 24(9): 1082-1095 (2015).

French, D. L., et al., "The influence of formulation on emission, deaggregation and deposition of dry powders for Inhalation" Journal of Aerosol Science 27(5): 769-783 (1996).

French, S., et al., "What is a conservative substitution?" Journal of Molecular Evolution 19: 171-175 (1983).

Gallop et al. "Applications of combinatorial technologies to drug discovery 1. Background and peptide combinatorial libraries" J Med Chem 37(9):1233-1251 (1994).

Gonda, I, et al. "Aerosols for delivery of therapeutic and diagnostic agents to the respiratory tract" Critical Reviews in Therapeutic Drug Carrier Systems 6:273-313 (1990).

Grewal, I. S., et al., CD40 and CD154 in cell-mediated immunity. Annu Rev Immunol. 16:111-135 (1998).

Grewal, I.S., et al., "The CD40-CD154 system in anti-infective host defense" Curr Opin Immunol. 9(4): 491-497 (1997).

Grewal, I.S., et al., "The role of CD40 ligand in costimulation and T-cell activation" Immunol Rev. 153: 85-106 (1996).

(56) References Cited

OTHER PUBLICATIONS

Gruss, H. J. , et al., "CD40/CD40 ligand interactions in normal, reactive and malignant lympho-hematopoietic tissues" Leuk Lymphoma. 24(5-6): 393-422 (1997).
Harris, R. J., et al., "Identification of multiple sources of charge heterogeneity in a recombinant antibody" J. Chromatogr. B Biomed. Sci. Appl. 2001; 752: 233-245.
Hering, B. J., et al., 'Prolonged diabetes reversal after intraportal xenotransplantation of wild-type porcine islets in mmunosuppressed nonhuman primates', Nature Medicine, vol. 12, No. 3, pp. 301-303. https://doi.org/10.1038/nm1369, 2006.
Hershfield, M.S., "Biochemistry and Immunology of Poly(ethylene glycol)-Modified Adenosine Deaminase (PEG-ADA). Poly(ethylene glycol)" Chapter 10, pp. 145-154 (1997).
Houghten, R. A., et al., "The use of synthetic peptide combinatorial libraries for the identification of bioactive peptides" Biotechniques 13(3):412-421 (1992).
International Search Report and Written Opinion for corresponding PCT Application No. PCT/NL2019/050086 issued Jul. 8, 2019.
Karimi, M.H., et al. Tolerance Induction by CD40 Blocking through Specific Antibody in Dendritic Cells. Iran J Allergy Asthma Immunol. Sep. 2010;9(3):141-7. PMID: 20952803.
Kawabe, T., et al., "CD40/CD40 ligand interactions in immune responses and pulmonary immunity" Nagoya J Med Sci. 73(3-4): 69-78 (2011).
Kobayashi, S., et al., "Pulmonary delivery of salmon calcitonin dry powders containing absorption enhancers in rats" Pharm Res. 13(1): 80-83 (1996).
Lam, K. S., "Application of Combinatorial Library Methods in Cancer Research and Drug Discovery" Anticancer Drug Des 12:145-167 (1997).
Lam, K. S., et al., "A new type of synthetic peptide library for identifying ligand-binding activity" Nature, 354:82-84 (1991).
Laman, J. D., et al., "CD40 in clinical inflammation: from multiple sclerosis to atherosclerosis" Dev Immunol 6(3-4): 215-222 (1998).
Limbach, P. A., et al., "Summary: the modified nucleosides of RNA." Nucleic acids research vol. 22, No. 12, pp. 2183-2196, 1994.
Lowe, M., et al., "A novel monoclonal antibody to CD40 prolongs islet allograft survival" Am J Transplant. 12(8): 2079-2087 (2012).
Mahajan, A., et al., "Structural Modification of Proteins and Peptides" Indian Journal of Pharmaceutical Education and Research, vol. 48, Issue 3, pp. 34-47, Jul.-Sep. 2014.
Mohiuddin, M. M., et al., "Chimeric 2010R4 anti-CD40 antibody therapy is critical for long-term survival of GTKO. hCD46.hTBM pig-to-primate cardiac xenograft" Nat Commun.7: 11138, 10 pages total (2016).
Mumtaz, S., et al. "Design of liposomes for circumventing the reticuloendothelial cells" Glycobiology 5:505-10 (1991).
Nakamura, Y., et al., "Codon usage tabulated from international DNA sequence databases: status for the year 2000" Nucleic Acids Res. Jan. 1, 2000; 28(1): 292.
Niven, R. W., et al., "The pulmonary absorption of aerosolized and intratracheally instilled rhG-CSF and monoPEGylated rhG-CSF" Pharm Res. 12(9): 1343-1349 (1995).
Noelle, R. J., et al., "CD40 and its ligand in autoimmunity" Ann N Y Acad Sci. 815: 384-391 (1997).
Noelle, R.J., "CD40 and its ligand in host defense" Immunity, 4(5): 415-419 (1996).
Obrezanova, Olga et al. "Aggregation risk prediction for antibodies and its application to biotherapeutic development." mAbs vol. 7,2 (2015): 352-63. doi: 10.1080/19420862.2015.1007828.
Olson, K., et al. "Preparation and Characterization of Poly(ethylene glycol)yated Human Growth Hormone Antagonist," in Poly(ethylene glycol) Chemistry & Biological Applications, 1997; Eds. JM Harris & S. Zalipsky; ACS, Washington, D.C., 170-181. (APP).
Oura, T, et al. Addition of Anti-CD40 Monoclonal Antibody to Nonmyeloablative Conditioning With Belatacept Abrogated Allograft Tolerance Despite Induction of Mixed Chimerism. Transplantation. Jan. 2019; 103(1):168-176. doi: 10.1097/TP.0000000000002417. PMID: 30113996; PMCID: PMC6309923.
Pagni, P. P., et al., "CD40-targeted peptide proposed for type 1 diabetes therapy lacks relevant binding affinity to its cognate receptor" Diabetologia. 62(9): 1727-1729 (2019).
Patton, J. S., et al., "(D) Routes of delivery: Case studies: (2) Pulmonary delivery of peptides and proteins for systemic action" Advanced Drug Delivery Reviews 8(2-3): 179-196 (1992).
Patton, J. S., et al. "Bioavailability of pulmonary delivered peptides and proteins: α-interferon, calcitonins and barathyroid hormones", Journal of Controlled Release 28(1-3):79-85 (1994).
Payne, R. W., et al., "Peptide Formulation: Challenges and Strategies—The properties of peptides make them particularly difficult to formulate but, with the right approach, they can be developed into effective therapies" Innovations in Pharmaceutical Technology. pp. 64-68 (2009).
Plebanski, M., et al., "Methods to measure T-cell responses" Expert Rev Vaccines. 9(6): 595-600 (2010).
Robinson, N. E., and Robinson, A. B., "Molecular Clocks: Deamidation of Asparaginyl and Glutaminyl Residues in Peptides and Proteins" Atlhouse Press, (2004), ISBN: 1590872509.
Rudt, S., et al., "In vitro phagocytosis assay of nano- and microparticles by chemiluminescence. I. Effect of analytical parameters, particle size and particle concentration" Journal of Controlled Release 22(3): 263-271 (1992).
Sali, A., et al., "Comparative protein modelling by satisfaction of spatial restraints" J Mol Biol. Dec. 5, 1993;234 (3):779-815. doi: 10.1006/jmbi.1993.162.
Scott, J. K., et al., "Searching For Peptide Ligands With an Epitope Library" Science 249:386-390 (1990).
Senhaji, N., et al., "The Contribution of CD40/CD40L Axis in Inflammatory Bowel Disease: An Update" Front Immunol.6: 529, pp. 1-6 (2015).
Su, K. Y., et al., "Efficient Culture of Human Naive and Memory B Cells for Use as APCs" J Immunol. 197(10): 4163-4176 (2016).
Sun, K. Y., et al., "Hydrophobic ion pairing of an insulin-sodium deoxycholate complex for oral delivery of insulin" Int J Nanomedicine. 6: 3049-3056 (2011).
Tabata, Y., et al., "Macrophage phagocytosis of biodegradable microspheres composed of L-lactic acid/glycolic acid homo- and copolymers" J Biomed Mater Res. 22(10): 837-858 (1988).
Taylor, W. R., "The classification of amino acid conservation" J Theor Biol. 119(2): 205-218 (1986).
Timsina, M. P., et al., "Drug delivery to the respiratory tract using dry powder inhalers" International Journal of Pharmaceutics 101(1-2): 1-13 (1994).
Uhlig, T., et al., "The emergence of peptides in the pharmaceutical business: From exploration to exploitation" EuPA Open Proteomics 4: 58-69 (2014).
Ui-Tei, K., et al., "Sensitive assay of RNA interference in *Drosophila* and Chinese hamster cultured cells using firefly luciferase gene as target" FEBS Lett, 479:79-82 (2000).
Ulysse, L., et al., "Photoregulation of cyclic peptide conformation" J Am Chem Soc 117:8466-8467 (1995).
Vaitaitis, G. M., et al., "A CD40-targeted peptide controls and reverses type 1 diabetes in NOD mice" Diabetologia. 57(11): 2366-2373 (2014).
Van Kooten, C., et al., "CD40-CD40 ligand" J Leukoc Biol. 67(1): 2-17 (2000).
Van Kooten, C., et al., "Functions of CD40 on B cells, dendritic cells and other cells" Curr Opin Immunol. 9(3): 330-337 (1997).
Verdini, A. S., et al., "Synthesis, resolution, and assignment of configuration of potent hypotensive retro-inverso bradykinin potentiating peptide 5a(BPP5a) analogues" J. Chem. Soc. Perkin Trans. 1(0): 697-701 (1985).
Visser, J., "An Invited Review: Van der Waals and other cohesive forces affecting powder fluidization" Powder Technology 58(1): 1-10 (1989).
Waddell, P. J., et al. "Towards resolving the interordinal relationships of placental mammals" Syst Biol Mar. 1999;48 (1):1-5.
Wall, D.A., "Pulmonary Absorption of Peptides and Proteins" Journal Drug Delivery 2(1): 1-20 (1995).
Xu, H., et al., "Effects of combined treatment with CD25- and CD154-specific monoclonal antibodies in non-human primate allotransplantation" Am J Transplant. 3(11): 1350-1354 (2003).

(56) References Cited

OTHER PUBLICATIONS

Yoshimori, A., et al., "Structure-based design of an agonistic peptide targeting Fas" Apoptosis. 10(2): 323-329 (2005).
Zanen, P., et al., "The optimal particle size for parasympathicolytic aerosols in mild asthmatics" International Journal of Pharmaceutics 114(1): 111-115 (1995).
Zuckermann, R. N., et al. "Discovery of nanomolar ligands for 7-transmembrane G-protein-coupled receptors from a DiverseN-(substituted)glycine peptoid library" J Med Chem 37(17):2678-2685 (1994).

* cited by examiner

Light chain variable region variants:

Heavy chain variable region variants:

A

B

SEQUENCE LISTING

<160> NUMBER OF SEQ ID NOS: 67

<210> SEQ ID NO 1
<211> LENGTH: 16
<212> TYPE: PRT
<213> ORGANISM: Artificial Sequence
<220> FEATURE:
<223> OTHER INFORMATION: CDR1 of anti-CD40 antibody
<220> FEATURE:
<221> NAME/KEY: VARIANT
<222> LOCATION: (10)..(10)
<223> OTHER INFORMATION: May be S or Q

<400> SEQUENCE: 1

Arg Ser Ser Gln Ser Leu Ala Ser Ser Xaa Gly Asn Thr Tyr Leu His
1 5 10 15

<210> SEQ ID NO 2
<211> LENGTH: 7
<212> TYPE: PRT
<213> ORGANISM: Artificial Sequence
<220> FEATURE:
<223> OTHER INFORMATION: CDR2 of anti-CD40 antibody

<400> SEQUENCE: 2

```
Lys Val Ser Asn Arg Phe Ser
1               5
```

<210> SEQ ID NO 3
<211> LENGTH: 9
<212> TYPE: PRT
<213> ORGANISM: Artificial Sequence
<220> FEATURE:
<223> OTHER INFORMATION: CDR3 of anti-CD40 antibody

<400> SEQUENCE: 3

```
Ser Gln Ser Thr His Val Pro Trp Thr
1               5
```

<210> SEQ ID NO 4
<211> LENGTH: 7
<212> TYPE: PRT
<213> ORGANISM: Artificial Sequence
<220> FEATURE:
<223> OTHER INFORMATION: CDR1 of anti-CD40 antibody
<220> FEATURE:
<221> NAME/KEY: VARIANT
<222> LOCATION: (4)..(4)
<223> OTHER INFORMATION: May be I or V

<400> SEQUENCE: 4

```
Gly Phe Ser Leu Ser Arg Tyr
1               5
```

<210> SEQ ID NO 5
<211> LENGTH: 7
<212> TYPE: PRT
<213> ORGANISM: Artificial Sequence
<220> FEATURE:
<223> OTHER INFORMATION: CDR2 of anti-CD40 antibody

<400> SEQUENCE: 5

```
Trp Gly Gly Gly Ser Thr Asp
1               5
```

<210> SEQ ID NO 6
<211> LENGTH: 5
<212> TYPE: PRT
<213> ORGANISM: Artificial Sequence
<220> FEATURE:
<223> OTHER INFORMATION: CDR3 of anti-CD40 antibody

<400> SEQUENCE: 6

```
Thr Asp Gly Asp Tyr
1               5
```

<210> SEQ ID NO 7
<211> LENGTH: 113
<212> TYPE: PRT
<213> ORGANISM: Artificial Sequence
<220> FEATURE:
<223> OTHER INFORMATION: anti-CD40 heavy chain variable region
<220> FEATURE:
<221> NAME/KEY: MISC_FEATURE
<222> LOCATION: (3)..(3)
<223> OTHER INFORMATION: is Q
<220> FEATURE:
<221> NAME/KEY: MISC_FEATURE
<222> LOCATION: (5)..(5)
<223> OTHER INFORMATION: is Q or V
<220> FEATURE:
<221> NAME/KEY: MISC_FEATURE
<222> LOCATION: (9)..(9)
<223> OTHER INFORMATION: is P or G
<220> FEATURE:
<221> NAME/KEY: MISC_FEATURE
<222> LOCATION: (15)..(15)
<223> OTHER INFORMATION: is S or G
<220> FEATURE:
<221> NAME/KEY: MISC_FEATURE
<222> LOCATION: (16)..(16)
<223> OTHER INFORMATION: is E, Q, or G
<220> FEATURE:
<221> NAME/KEY: MISC_FEATURE
<222> LOCATION: (17)..(17)
<223> OTHER INFORMATION: is T or S
<220> FEATURE:
<221> NAME/KEY: MISC_FEATURE
<222> LOCATION: (19)..(19)
<223> OTHER INFORMATION: is S or R
<220> FEATURE:
<221> NAME/KEY: MISC_FEATURE
<222> LOCATION: (20)..(20)
<223> OTHER INFORMATION: is I or L
<220> FEATURE:
<221> NAME/KEY: MISC_FEATURE
<222> LOCATION: (21)..(21)
<223> OTHER INFORMATION: is T or S
<220> FEATURE:
<221> NAME/KEY: MISC_FEATURE
<222> LOCATION: (23)..(23)
<223> OTHER INFORMATION: is T or A
<220> FEATURE:
<221> NAME/KEY: MISC_FEATURE
<222> LOCATION: (29)..(29)
<223> OTHER INFORMATION: is I, L, or V
<220> FEATURE:
<221> NAME/KEY: MISC_FEATURE
<222> LOCATION: (37)..(37)
<223> OTHER INFORMATION: is I, L, or V
<220> FEATURE:
<221> NAME/KEY: MISC_FEATURE
<222> LOCATION: (40)..(40)
<223> OTHER INFORMATION: is P or A
<220> FEATURE:
<221> NAME/KEY: MISC_FEATURE
<222> LOCATION: (45)..(45)
<223> OTHER INFORMATION: is P or L
<220> FEATURE:
<221> NAME/KEY: MISC_FEATURE
<222> LOCATION: (48)..(48)
<223> OTHER INFORMATION: is M or I
<220> FEATURE:
<221> NAME/KEY: MISC_FEATURE
<222> LOCATION: (60)..(61)
<223> OTHER INFORMATION: is ST or NP
<220> FEATURE:
<221> NAME/KEY: MISC_FEATURE
<222> LOCATION: (63)..(63)
<223> OTHER INFORMATION: is L or V
<220> FEATURE:
<221> NAME/KEY: MISC_FEATURE
<222> LOCATION: (65)..(65)
<223> OTHER INFORMATION: is S or G
<220> FEATURE:
<221> NAME/KEY: MISC_FEATURE
<222> LOCATION: (67)..(67)
<223> OTHER INFORMATION: is L or F
<220> FEATURE:
<221> NAME/KEY: MISC_FEATURE
<222> LOCATION: (73)..(73)
<223> OTHER INFORMATION: is T or N
<220> FEATURE:
<221> NAME/KEY: MISC_FEATURE
<222> LOCATION: (74)..(74)
<223> OTHER INFORMATION: is S or A
<220> FEATURE:
<221> NAME/KEY: MISC_FEATURE
<222> LOCATION: (76)..(76)
<223> OTHER INFORMATION: is S or T
<220> FEATURE:

<221> NAME/KEY: MISC_FEATURE
<222> LOCATION: (77)..(77)
<223> OTHER INFORMATION: is Q or S
<220> FEATURE:
<221> NAME/KEY: MISC_FEATURE
<222> LOCATION: (79)..(79)
<223> OTHER INFORMATION: is S or Y
<220> FEATURE:
<221> NAME/KEY: MISC_FEATURE
<222> LOCATION: (81)..(81)
<223> OTHER INFORMATION: is K or Q
<220> FEATURE:
<221> NAME/KEY: MISC_FEATURE
<222> LOCATION: (82)..(82)
<223> OTHER INFORMATION: is M or L
<220> FEATURE:
<221> NAME/KEY: MISC_FEATURE
<222> LOCATION: (83)..(83)
<223> OTHER INFORMATION: is S
<220> FEATURE:
<221> NAME/KEY: MISC_FEATURE
<222> LOCATION: (86)..(86)
<223> OTHER INFORMATION: is R or T
<220> FEATURE:
<221> NAME/KEY: MISC_FEATURE
<222> LOCATION: (87)..(87)
<223> OTHER INFORMATION: is A
<220> FEATURE:
<221> NAME/KEY: MISC_FEATURE
<222> LOCATION: (88)..(88)
<223> OTHER INFORMATION: is A or E
<220> FEATURE:
<221> NAME/KEY: MISC_FEATURE
<222> LOCATION: (92)..(92)
<223> OTHER INFORMATION: is V
<220> FEATURE:
<221> NAME/KEY: MISC_FEATURE
<222> LOCATION: (108)..(108)
<223> OTHER INFORMATION: is L

<400> SEQUENCE: 7

```
Gln Val Xaa Leu Xaa Glu Ser Gly Xaa Gly Leu Val Lys Pro Xaa Xaa
1               5                   10                  15

Xaa Leu Xaa Xaa Xaa Cys Xaa Val Ser Gly Phe Ser Xaa Ser Arg Tyr
            20                  25                  30

Ser Val Tyr Trp Xaa Arg Gln Xaa Pro Gly Lys Gly Xaa Glu Trp Xaa
        35                  40                  45

Gly Met Met Trp Gly Gly Gly Ser Thr Asp Tyr Xaa Xaa Ser Xaa Lys
    50                  55                  60

Xaa Arg Xaa Thr Ile Ser Lys Asp Xaa Xaa Lys Xaa Xaa Val Xaa Leu
65                  70                  75                  80

Xaa Xaa Xaa Ser Leu Xaa Xaa Xaa Asp Thr Ala Xaa Tyr Tyr Cys Val
                85                  90                  95

Arg Thr Asp Gly Asp Tyr Trp Gly Gln Gly Thr Xaa Val Thr Val Ser
            100                 105                 110

Ser
```

<210> SEQ ID NO 8
<211> LENGTH: 113
<212> TYPE: PRT
<213> ORGANISM: Artificial Sequence
<220> FEATURE:
<223> OTHER INFORMATION: anti CD40 light chain variable region
<220> FEATURE:
<221> NAME/KEY: MISC_FEATURE
<222> LOCATION: (1)..(4)
<223> OTHER INFORMATION: is ELQL or DIVM
<220> FEATURE:
<221> NAME/KEY: MISC_FEATURE
<222> LOCATION: (15)..(15)

<223> OTHER INFORMATION: is L or P
<220> FEATURE:
<221> NAME/KEY: MISC_FEATURE
<222> LOCATION: (31)..(31)
<223> OTHER INFORMATION: is S or D
<220> FEATURE:
<221> NAME/KEY: MISC_FEATURE
<222> LOCATION: (33)..(33)
<223> OTHER INFORMATION: is S or Q
<220> FEATURE:
<221> NAME/KEY: MISC_FEATURE
<222> LOCATION: (44)..(44)
<223> OTHER INFORMATION: is R or K

<400> SEQUENCE: 8

```
Xaa Xaa Xaa Xaa Thr Gln Ser Pro Leu Ser Leu Pro Val Thr Xaa Gly
1               5                   10                  15

Gln Pro Ala Ser Ile Ser Cys Arg Ser Ser Gln Ser Leu Ala Xaa Ser
            20                  25                  30

Xaa Gly Asn Thr Tyr Leu His Trp Tyr Leu Gln Xaa Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gly Gly Thr Lys Leu Glu Ile Lys
            100                 105                 110

Arg
```

<210> SEQ ID NO 9
<211> LENGTH: 4
<212> TYPE: PRT
<213> ORGANISM: Artificial Sequence
<220> FEATURE:
<223> OTHER INFORMATION: Optional sequence Z1, Z2, Z3 and Z4

<400> SEQUENCE: 9

```
Glu Leu Gln Leu
1
```

<210> SEQ ID NO 10
<211> LENGTH: 4
<212> TYPE: PRT
<213> ORGANISM: Artificial Sequence
<220> FEATURE:
<223> OTHER INFORMATION: Optional sequence Z1, Z2, Z3 and Z4

<400> SEQUENCE: 10

```
Asp Ile Val Met
1
```

<210> SEQ ID NO 11
<211> LENGTH: 16
<212> TYPE: PRT
<213> ORGANISM: Artificial Sequence
<220> FEATURE:
<223> OTHER INFORMATION: VL-CDR1A

<400> SEQUENCE: 11

```
Arg Ser Ser Gln Ser Leu Ala Ser Ser Ser Gly Asn Thr Tyr Leu His
1               5                   10                  15
```

<210> SEQ ID NO 12
<211> LENGTH: 16
<212> TYPE: PRT
<213> ORGANISM: Artificial Sequence
<220> FEATURE:
<223> OTHER INFORMATION: VL-CDR1B

<400> SEQUENCE: 12

```
Arg Ser Ser Gln Ser Leu Ala Ser Ser Gln Gly Asn Thr Tyr Leu His
1               5                   10                  15
```

<210> SEQ ID NO 13
<211> LENGTH: 7
<212> TYPE: PRT
<213> ORGANISM: Artificial Sequence
<220> FEATURE:
<223> OTHER INFORMATION: VL-CDR2

<400> SEQUENCE: 13

```
Lys Val Ser Asn Arg Phe Ser
1               5
```

<210> SEQ ID NO 14
<211> LENGTH: 9
<212> TYPE: PRT
<213> ORGANISM: Artificial Sequence
<220> FEATURE:
<223> OTHER INFORMATION: VL-CDR3

<400> SEQUENCE: 14

```
Ser Gln Ser Thr His Val Pro Trp Thr
1               5
```

<210> SEQ ID NO 15
<211> LENGTH: 23
<212> TYPE: PRT
<213> ORGANISM: Artificial Sequence
<220> FEATURE:
<223> OTHER INFORMATION: VL-FR1A

<400> SEQUENCE: 15

```
Glu Leu Gln Leu Thr Gln Ser Pro Leu Ser Leu Pro Val Thr Leu Gly
1               5                   10                  15

Gln Pro Ala Ser Ile Ser Cys
            20
```

<210> SEQ ID NO 16
<211> LENGTH: 23
<212> TYPE: PRT
<213> ORGANISM: Artificial Sequence
<220> FEATURE:
<223> OTHER INFORMATION: VL-FR1B

<400> SEQUENCE: 16

```
Asp Ile Val Met Thr Gln Ser Pro Leu Ser Leu Pro Val Thr Pro Gly
1               5                   10                  15

Gln Pro Ala Ser Ile Ser Cys
            20
```

<210> SEQ ID NO 17
<211> LENGTH: 15
<212> TYPE: PRT
<213> ORGANISM: Artificial Sequence
<220> FEATURE:
<223> OTHER INFORMATION: VL-FR2A

<400> SEQUENCE: 17

```
Trp Tyr Leu Gln Arg Pro Gly Gln Ser Pro Arg Leu Leu Ile Tyr
1               5                   10                  15


<210> SEQ ID NO 18
<211> LENGTH: 15
<212> TYPE: PRT
<213> ORGANISM: Artificial Sequence
<220> FEATURE:
<223> OTHER INFORMATION: VL-FR2B

<400> SEQUENCE: 18

Trp Tyr Leu Gln Lys Pro Gly Gln Ser Pro Arg Leu Leu Ile Tyr
1               5                   10                  15


<210> SEQ ID NO 19
<211> LENGTH: 32
<212> TYPE: PRT
<213> ORGANISM: Artificial Sequence
<220> FEATURE:
<223> OTHER INFORMATION: VL-FR3

<400> SEQUENCE: 19

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30


<210> SEQ ID NO 20
<211> LENGTH: 11
<212> TYPE: PRT
<213> ORGANISM: Artificial Sequence
<220> FEATURE:
<223> OTHER INFORMATION: VL-FR4

<400> SEQUENCE: 20

Phe Gly Gly Gly Thr Lys Leu Glu Ile Lys Arg
1               5                   10


<210> SEQ ID NO 21
<211> LENGTH: 113
<212> TYPE: PRT
<213> ORGANISM: Artificial Sequence
<220> FEATURE:
<223> OTHER INFORMATION: VL-1

<400> SEQUENCE: 21

Glu Leu Gln Leu Thr Gln Ser Pro Leu Ser Leu Pro Val Thr Leu Gly
1               5                   10                  15

Gln Pro Ala Ser Ile Ser Cys Arg Ser Ser Gln Ser Leu Ala Ser Ser
            20                  25                  30

Ser Gly Asn Thr Tyr Leu His Trp Tyr Leu Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gly Gly Thr Lys Leu Glu Ile Lys
            100                 105                 110

Arg
```

<210> SEQ ID NO 22
<211> LENGTH: 113
<212> TYPE: PRT
<213> ORGANISM: Artificial Sequence
<220> FEATURE:
<223> OTHER INFORMATION: VL-2

<400> SEQUENCE: 22

```
Glu Leu Gln Leu Thr Gln Ser Pro Leu Ser Leu Pro Val Thr Leu Gly
1               5                   10                  15

Gln Pro Ala Ser Ile Ser Cys Arg Ser Ser Gln Ser Leu Ala Ser Ser
            20                  25                  30

Gln Gly Asn Thr Tyr Leu His Trp Tyr Leu Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gly Gly Thr Lys Leu Glu Ile Lys
            100                 105                 110

Arg
```

<210> SEQ ID NO 23
<211> LENGTH: 113
<212> TYPE: PRT
<213> ORGANISM: Artificial Sequence
<220> FEATURE:
<223> OTHER INFORMATION: VL-4

<400> SEQUENCE: 23

```
Asp Ile Val Met Thr Gln Ser Pro Leu Ser Leu Pro Val Thr Pro Gly
1               5                   10                  15

Gln Pro Ala Ser Ile Ser Cys Arg Ser Ser Gln Ser Leu Ala Ser Ser
            20                  25                  30

Gln Gly Asn Thr Tyr Leu His Trp Tyr Leu Gln Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gly Gly Thr Lys Leu Glu Ile Lys
            100                 105                 110

Arg
```

<210> SEQ ID NO 24
<211> LENGTH: 7
<212> TYPE: PRT
<213> ORGANISM: Artificial Sequence
<220> FEATURE:
<223> OTHER INFORMATION: VH-CDR1A

<400> SEQUENCE: 24

```
Gly Phe Ser Leu Ser Arg Tyr
1               5
```

<210> SEQ ID NO 25
<211> LENGTH: 7
<212> TYPE: PRT
<213> ORGANISM: Artificial Sequence
<220> FEATURE:
<223> OTHER INFORMATION: VH-CDR1B

<400> SEQUENCE: 25

```
Gly Phe Ser Ile Ser Arg Tyr
1               5
```

<210> SEQ ID NO 26
<211> LENGTH: 7
<212> TYPE: PRT
<213> ORGANISM: Artificial Sequence
<220> FEATURE:
<223> OTHER INFORMATION: VH-CDR1C

<400> SEQUENCE: 26

```
Gly Phe Ser Val Ser Arg Tyr
1               5
```

<210> SEQ ID NO 27
<211> LENGTH: 7
<212> TYPE: PRT
<213> ORGANISM: Artificial Sequence
<220> FEATURE:
<223> OTHER INFORMATION: VH-CDR2

<400> SEQUENCE: 27

```
Trp Gly Gly Gly Ser Thr Asp
1               5
```

<210> SEQ ID NO 28
<211> LENGTH: 5
<212> TYPE: PRT
<213> ORGANISM: Artificial Sequence
<220> FEATURE:
<223> OTHER INFORMATION: VH-CDR3

<400> SEQUENCE: 28

```
Thr Asp Gly Asp Tyr
1               5
```

<210> SEQ ID NO 29
<211> LENGTH: 25
<212> TYPE: PRT
<213> ORGANISM: Artificial Sequence
<220> FEATURE:
<223> OTHER INFORMATION: VH-FR1A

<400> SEQUENCE: 29

```
Gln Val Gln Leu Gln Glu Ser Gly Pro Gly Leu Val Lys Pro Ser Glu
1               5                   10                  15

Thr Leu Ser Ile Thr Cys Thr Val Ser
            20                  25
```

<210> SEQ ID NO 30
<211> LENGTH: 25
<212> TYPE: PRT
<213> ORGANISM: Artificial Sequence
<220> FEATURE:
<223> OTHER INFORMATION: VH-FR1B

<400> SEQUENCE: 30

```
Gln Val Gln Leu Gln Glu Ser Gly Pro Gly Leu Val Lys Pro Ser Gln
```

1 5 10 15

Thr Leu Ser Leu Thr Cys Thr Val Ser
20 25

<210> SEQ ID NO 31
<211> LENGTH: 25
<212> TYPE: PRT
<213> ORGANISM: Artificial Sequence
<220> FEATURE:
<223> OTHER INFORMATION: VH-FR1C

<400> SEQUENCE: 31

Gln Val Gln Leu Val Glu Ser Gly Gly Gly Leu Val Lys Pro Gly Gly
1 5 10 15

Ser Leu Arg Leu Ser Cys Ala Val Ser
20 25

<210> SEQ ID NO 32
<211> LENGTH: 19
<212> TYPE: PRT
<213> ORGANISM: Artificial Sequence
<220> FEATURE:
<223> OTHER INFORMATION: VH-FR2A

<400> SEQUENCE: 32

Ser Val Tyr Trp Ile Arg Gln Pro Pro Gly Lys Gly Pro Glu Trp Met
1 5 10 15

Gly Met Met

<210> SEQ ID NO 33
<211> LENGTH: 19
<212> TYPE: PRT
<213> ORGANISM: Artificial Sequence
<220> FEATURE:
<223> OTHER INFORMATION: VH-FR2B

<400> SEQUENCE: 33

Ser Val Tyr Trp Val Arg Gln Pro Pro Gly Lys Gly Leu Glu Trp Met
1 5 10 15

Gly Met Met

<210> SEQ ID NO 34
<211> LENGTH: 19
<212> TYPE: PRT
<213> ORGANISM: Artificial Sequence
<220> FEATURE:
<223> OTHER INFORMATION: VH-FR2C

<400> SEQUENCE: 34

Ser Val Tyr Trp Val Arg Gln Pro Pro Gly Lys Gly Leu Glu Trp Ile
1 5 10 15

Gly Met Met

<210> SEQ ID NO 35
<211> LENGTH: 19
<212> TYPE: PRT
<213> ORGANISM: Artificial Sequence
<220> FEATURE:
<223> OTHER INFORMATION: VH-FR2D

<400> SEQUENCE: 35

Ser Val Tyr Trp Ile Arg Gln Ala Pro Gly Lys Gly Leu Glu Trp Met
1 5 10 15

```
Gly Met Met


<210> SEQ ID NO 36
<211> LENGTH: 39
<212> TYPE: PRT
<213> ORGANISM: Artificial Sequence
<220> FEATURE:
<223> OTHER INFORMATION: VH-FR3A

<400> SEQUENCE: 36

Tyr Ser Thr Ser Leu Lys Ser Arg Leu Thr Ile Ser Lys Asp Thr Ser
1               5                   10                  15

Lys Ser Gln Val Ser Leu Lys Met Ser Ser Leu Thr Ala Ala Asp Thr
            20                  25                  30

Ala Val Tyr Tyr Cys Val Arg
        35


<210> SEQ ID NO 37
<211> LENGTH: 39
<212> TYPE: PRT
<213> ORGANISM: Artificial Sequence
<220> FEATURE:
<223> OTHER INFORMATION: VH-FR3B

<400> SEQUENCE: 37

Tyr Asn Pro Ser Leu Lys Ser Arg Leu Thr Ile Ser Lys Asp Thr Ser
1               5                   10                  15

Lys Ser Gln Val Ser Leu Lys Leu Ser Ser Leu Thr Ala Ala Asp Thr
            20                  25                  30

Ala Val Tyr Tyr Cys Val Arg
        35


<210> SEQ ID NO 38
<211> LENGTH: 39
<212> TYPE: PRT
<213> ORGANISM: Artificial Sequence
<220> FEATURE:
<223> OTHER INFORMATION: VH-FR3C

<400> SEQUENCE: 38

Tyr Ser Thr Ser Val Lys Gly Arg Phe Thr Ile Ser Lys Asp Asn Ala
1               5                   10                  15

Lys Thr Ser Val Tyr Leu Gln Met Ser Ser Leu Arg Ala Glu Asp Thr
            20                  25                  30

Ala Val Tyr Tyr Cys Val Arg
        35


<210> SEQ ID NO 39
<211> LENGTH: 11
<212> TYPE: PRT
<213> ORGANISM: Artificial Sequence
<220> FEATURE:
<223> OTHER INFORMATION: VH-FR4

<400> SEQUENCE: 39

Trp Gly Gln Gly Thr Leu Val Thr Val Ser Ser
1               5                   10


<210> SEQ ID NO 40
<211> LENGTH: 113
<212> TYPE: PRT
<213> ORGANISM: Artificial Sequence
<220> FEATURE:
<223> OTHER INFORMATION: VH-1
```

<400> SEQUENCE: 40

```
Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Ser Arg Tyr
            20                  25                  30

Ser Val Tyr Trp Ile Arg Gln Pro Pro Gly Lys Gly Pro Glu Trp Met
        35                  40                  45

Gly Met Met Trp Gly Gly Gly Ser Thr Asp Tyr Ser Thr Ser Leu Lys
    50                  55                  60

Ser Arg Leu Thr Ile Ser Lys Asp Thr Ser Lys Ser Gln Val Ser Leu
65                  70                  75                  80

Lys Met Ser Ser Leu Thr Ala Ala Asp Thr Ala Val Tyr Tyr Cys Val
                85                  90                  95

Arg Thr Asp Gly Asp Tyr Trp Gly Gln Gly Thr Leu Val Thr Val Ser
            100                 105                 110

Ser
```

<210> SEQ ID NO 41
<211> LENGTH: 113
<212> TYPE: PRT
<213> ORGANISM: Artificial Sequence
<220> FEATURE:
<223> OTHER INFORMATION: VH_2

<400> SEQUENCE: 41

```
Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Ser Arg Tyr
            20                  25                  30

Ser Val Tyr Trp Val Arg Gln Pro Pro Gly Lys Gly Leu Glu Trp Met
        35                  40                  45

Gly Met Met Trp Gly Gly Gly Ser Thr Asp Tyr Ser Thr Ser Leu Lys
    50                  55                  60

Ser Arg Leu Thr Ile Ser Lys Asp Thr Ser Lys Ser Gln Val Ser Leu
65                  70                  75                  80

Lys Met Ser Ser Leu Thr Ala Ala Asp Thr Ala Val Tyr Tyr Cys Val
                85                  90                  95

Arg Thr Asp Gly Asp Tyr Trp Gly Gln Gly Thr Leu Val Thr Val Ser
            100                 105                 110

Ser
```

<210> SEQ ID NO 42
<211> LENGTH: 113
<212> TYPE: PRT
<213> ORGANISM: Artificial Sequence
<220> FEATURE:
<223> OTHER INFORMATION: VH-3

<400> SEQUENCE: 42

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Leu Ser Arg Tyr
            20                  25                  30

Ser Val Tyr Trp Val Arg Gln Pro Pro Gly Lys Gly Leu Glu Trp Ile
        35                  40                  45

Gly Met Met Trp Gly Gly Gly Ser Thr Asp Tyr Asn Pro Ser Leu Lys
```

```
    50                  55                  60

Ser Arg Leu Thr Ile Ser Lys Asp Thr Ser Lys Ser Gln Val Ser Leu
65                  70                  75                  80

Lys Leu Ser Ser Leu Thr Ala Ala Asp Thr Ala Val Tyr Tyr Cys Val
                85                  90                  95

Arg Thr Asp Gly Asp Tyr Trp Gly Gln Gly Thr Leu Val Thr Val Ser
            100                 105                 110

Ser


<210> SEQ ID NO 43
<211> LENGTH: 113
<212> TYPE: PRT
<213> ORGANISM: Artificial Sequence
<220> FEATURE:
<223> OTHER INFORMATION: VH-4

<400> SEQUENCE: 43

Gln Val Gln Leu Val Glu Ser Gly Gly Gly Leu Val Lys Pro Gly Gly
1               5                   10                  15

Ser Leu Arg Leu Ser Cys Ala Val Ser Gly Phe Ser Leu Ser Arg Tyr
            20                  25                  30

Ser Val Tyr Trp Ile Arg Gln Ala Pro Gly Lys Gly Leu Glu Trp Met
        35                  40                  45

Gly Met Met Trp Gly Gly Gly Ser Thr Asp Tyr Ser Thr Ser Val Lys
    50                  55                  60

Gly Arg Phe Thr Ile Ser Lys Asp Asn Ala Lys Thr Ser Val Tyr Leu
65                  70                  75                  80

Gln Met Ser Ser Leu Arg Ala Glu Asp Thr Ala Val Tyr Tyr Cys Val
                85                  90                  95

Arg Thr Asp Gly Asp Tyr Trp Gly Gln Gly Thr Leu Val Thr Val Ser
            100                 105                 110

Ser


<210> SEQ ID NO 44
<211> LENGTH: 5
<212> TYPE: PRT
<213> ORGANISM: Artificial Sequence
<220> FEATURE:
<223> OTHER INFORMATION: tryptic peptide H10

<400> SEQUENCE: 44

Met Asn Ser Leu Arg
1               5


<210> SEQ ID NO 45
<211> LENGTH: 26
<212> TYPE: PRT
<213> ORGANISM: Artificial Sequence
<220> FEATURE:
<223> OTHER INFORMATION: Tryptic peptide L2

<400> SEQUENCE: 45

Ser Ser Gln Ser Leu Ala Asn Ser Asn Gly Asn Thr Tyr Leu His Trp
1               5                   10                  15

Tyr Leu Gln Arg Pro Gly Gln Ser Pro Arg
            20                  25


<210> SEQ ID NO 46
<211> LENGTH: 239
<212> TYPE: PRT
```

```
<213> ORGANISM: Artificial Sequence
<220> FEATURE:
<223> OTHER INFORMATION: PG102_VL

<400> SEQUENCE: 46

Met Ser Val Pro Thr Gln Val Leu Gly Leu Leu Leu Leu Trp Leu Thr
1               5                   10                  15

Asp Ala Arg Cys Glu Leu Gln Leu Thr Gln Ser Pro Leu Ser Leu Pro
            20                  25                  30

Val Thr Leu Gly Gln Pro Ala Ser Ile Ser Cys Arg Ser Ser Gln Ser
        35                  40                  45

Leu Ala Asn Ser Asn Gly Asn Thr Tyr Leu His Trp Tyr Leu Gln Arg
    50                  55                  60

Pro Gly Gln Ser Pro Arg Leu Leu Ile Tyr Lys Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Ser Gln Ser Thr His Val Pro Trp Thr Phe Gly Gly Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235


<210> SEQ ID NO 47
<211> LENGTH: 239
<212> TYPE: PRT
<213> ORGANISM: Artificial Sequence
<220> FEATURE:
<223> OTHER INFORMATION: PG102_VL_1

<400> SEQUENCE: 47

Met Ser Val Pro Thr Gln Val Leu Gly Leu Leu Leu Leu Trp Leu Thr
1               5                   10                  15

Asp Ala Arg Cys Glu Leu Gln Leu Thr Gln Ser Pro Leu Ser Leu Pro
            20                  25                  30

Val Thr Leu Gly Gln Pro Ala Ser Ile Ser Cys Arg Ser Ser Gln Ser
        35                  40                  45

Leu Ala Ser Ser Ser Gly Asn Thr Tyr Leu His Trp Tyr Leu Gln Arg
    50                  55                  60

Pro Gly Gln Ser Pro Arg Leu Leu Ile Tyr Lys Val Ser Asn Arg Phe
65                  70                  75                  80

Ser Gly Val Pro Asp Arg Phe Ser Gly Ser Gly Ser Gly Thr Asp Phe
                85                  90                  95
```

```
Thr Leu Lys Ile Ser Arg Val Glu Ala Glu Asp Val Gly Val Tyr Tyr
            100                 105                 110

Cys Ser Gln Ser Thr His Val Pro Trp Thr Phe Gly Gly Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235


<210> SEQ ID NO 48
<211> LENGTH: 239
<212> TYPE: PRT
<213> ORGANISM: Artificial Sequence
<220> FEATURE:
<223> OTHER INFORMATION: PG102_VL_2

<400> SEQUENCE: 48

Met Ser Val Pro Thr Gln Val Leu Gly Leu Leu Leu Leu Trp Leu Thr
1               5                   10                  15

Asp Ala Arg Cys Glu Leu Gln Leu Thr Gln Ser Pro Leu Ser Leu Pro
            20                  25                  30

Val Thr Leu Gly Gln Pro Ala Ser Ile Ser Cys Arg Ser Ser Gln Ser
        35                  40                  45

Leu Ala Ser Ser Gln Gly Asn Thr Tyr Leu His Trp Tyr Leu Gln Arg
    50                  55                  60

Pro Gly Gln Ser Pro Arg Leu Leu Ile Tyr Lys Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Ser Gln Ser Thr His Val Pro Trp Thr Phe Gly Gly Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220
```

```
Gly Leu Ser Ser Pro Val Thr Lys Ser Phe Asn Arg Gly Glu Cys
225                 230                 235


<210> SEQ ID NO 49
<211> LENGTH: 239
<212> TYPE: PRT
<213> ORGANISM: Artificial Sequence
<220> FEATURE:
<223> OTHER INFORMATION: PG102_VL_3

<400> SEQUENCE: 49

Met Ser Val Pro Thr Gln Val Leu Gly Leu Leu Leu Leu Trp Leu Thr
1               5                   10                  15

Asp Ala Arg Cys Glu Leu Gln Leu Thr Gln Ser Pro Leu Ser Leu Pro
            20                  25                  30

Val Thr Leu Gly Gln Pro Ala Ser Ile Ser Cys Arg Ser Ser Gln Ser
        35                  40                  45

Leu Ala Asp Ser Gln Gly Asn Thr Tyr Leu His Trp Tyr Leu Gln Arg
    50                  55                  60

Pro Gly Gln Ser Pro Arg Leu Leu Ile Tyr Lys Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Ser Gln Ser Thr His Val Pro Trp Thr Phe Gly Gly Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235


<210> SEQ ID NO 50
<211> LENGTH: 239
<212> TYPE: PRT
<213> ORGANISM: Artificial Sequence
<220> FEATURE:
<223> OTHER INFORMATION: PG102_VL_4

<400> SEQUENCE: 50

Met Ser Val Pro Thr Gln Val Leu Gly Leu Leu Leu Leu Trp Leu Thr
1               5                   10                  15

Asp Ala Arg Cys Asp Ile Val Met Thr Gln Ser Pro Leu Ser Leu Pro
            20                  25                  30

Val Thr Pro Gly Gln Pro Ala Ser Ile Ser Cys Arg Ser Ser Gln Ser
        35                  40                  45

Leu Ala Ser Ser Gln Gly Asn Thr Tyr Leu His Trp Tyr Leu Gln Lys
    50                  55                  60
```

```
Pro Gly Gln Ser Pro Arg Leu Leu Ile Tyr Lys Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Ser Gln Ser Thr His Val Pro Trp Thr Phe Gly Gly Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

```
<210> SEQ ID NO 51
<211> LENGTH: 239
<212> TYPE: PRT
<213> ORGANISM: Artificial Sequence
<220> FEATURE:
<223> OTHER INFORMATION: PG102_VL_5

<400> SEQUENCE: 51

Met Ser Val Pro Thr Gln Val Leu Gly Leu Leu Leu Leu Trp Leu Thr
1               5                   10                  15

Asp Ala Arg Cys Asp Ile Val Met Thr Gln Ser Pro Leu Ser Leu Pro
            20                  25                  30

Val Thr Pro Gly Gln Pro Ala Ser Ile Ser Cys Arg Ser Ser Gln Ser
        35                  40                  45

Leu Ala Ala Ser Ala Gly Ala Thr Tyr Leu His Trp Tyr Leu Glu Lys
    50                  55                  60

Pro Gly Gln Pro Pro Arg Arg Leu Ile Tyr Lys Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Ser Gln Ser Thr His Val Pro Trp Thr Phe Gly Gly Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190
```

```
Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235


<210> SEQ ID NO 52
<211> LENGTH: 458
<212> TYPE: PRT
<213> ORGANISM: Artificial Sequence
<220> FEATURE:
<223> OTHER INFORMATION: PG102_VH

<400> SEQUENCE: 52

Met Glu Trp Ser Trp Val Phe Leu Phe Phe Leu Ser Val Thr Thr Gly
1               5                   10                  15

Val His Ser Gln Val Lys Leu Gln Glu Ser Gly Pro Gly Leu Val Lys
            20                  25                  30

Pro Ser Glu Thr Leu Ser Ile Thr Cys Thr Val Ser Gly Phe Ser Leu
        35                  40                  45

Ser Arg Tyr Ser Val Tyr Trp Ile Arg Gln Pro Pro Gly Lys Gly Pro
    50                  55                  60

Glu Trp Met Gly Met Met Trp Gly Gly Gly Ser Thr Asp Tyr Ser Thr
65                  70                  75                  80

Ser Leu Lys Ser Arg Leu Thr Ile Ser Lys Asp Thr Ser Lys Ser Gln
                85                  90                  95

Val Ser Leu Lys Met Asn Ser Leu Arg Thr Asp Asp Thr Ala Met Tyr
            100                 105                 110

Tyr Cys Val Arg Thr Asp Gly Asp Tyr Trp Gly Gln Gly Thr Thr Val
        115                 120                 125

Thr Val Ser Ser Ala Ser Thr Lys Gly Pro Ser Val Phe Pro Leu Ala
    130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Lys Thr Tyr Thr Cys Asn Val Asp His Lys Pro Ser Asn Thr
    210                 215                 220

Lys Val Asp Lys Arg Val Glu Ser Lys Tyr Gly Pro Pro Cys Pro Pro
225                 230                 235                 240

Cys Pro Ala Pro Glu Phe Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser Gln Glu Asp Pro Glu Val Gln Phe Asn
        275                 280                 285

Trp Tyr Val Asp Gly Val Glu Val His Asn Ala Lys Thr Lys Pro Arg
    290                 295                 300

Glu Glu Gln Phe Asn Ser Thr Tyr Arg Val Val Ser Val Leu Thr Val
305                 310                 315                 320
```

```
Leu His Gln Asp Trp Leu Asn Gly Lys Glu Tyr Lys Cys Lys Val Ser
                325                 330                 335

Asn Lys Gly Leu Pro Ser Ser Ile Glu Lys Thr Ile Ser Lys Ala Lys
            340                 345                 350

Gly Gln Pro Arg Glu Pro Gln Val Tyr Thr Leu Pro Pro Ser Gln Glu
        355                 360                 365

Glu Met Thr Lys Asn Gln Val Ser Leu Thr Cys Leu Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Arg Leu Thr Val Asp Lys Ser Arg Trp Gln Glu Gly
            420                 425                 430

Asn Val Phe Ser Cys Ser Val Met His Glu Ala Leu His Asn His Tyr
        435                 440                 445

Thr Gln Lys Ser Leu Ser Leu Ser Leu Gly
    450                 455


<210> SEQ ID NO 53
<211> LENGTH: 458
<212> TYPE: PRT
<213> ORGANISM: Artificial Sequence
<220> FEATURE:
<223> OTHER INFORMATION: PG102_VH_1

<400> SEQUENCE: 53

Met Glu Trp Ser Trp Val Phe Leu Phe Phe Leu Ser Val Thr Thr Gly
1               5                   10                  15

Val His Ser Gln Val Gln Leu Gln Glu Ser Gly Pro Gly Leu Val Lys
            20                  25                  30

Pro Ser Glu Thr Leu Ser Ile Thr Cys Thr Val Ser Gly Phe Ser Leu
        35                  40                  45

Ser Arg Tyr Ser Val Tyr Trp Ile Arg Gln Pro Pro Gly Lys Gly Pro
    50                  55                  60

Glu Trp Met Gly Met Met Trp Gly Gly Gly Ser Thr Asp Tyr Ser Thr
65                  70                  75                  80

Ser Leu Lys Ser Arg Leu Thr Ile Ser Lys Asp Thr Ser Lys Ser Gln
                85                  90                  95

Val Ser Leu Lys Met Ser Ser Leu Thr Ala Ala Asp Thr Ala Val Tyr
            100                 105                 110

Tyr Cys Val Arg Thr Asp Gly Asp Tyr Trp Gly Gln Gly Thr Leu Val
        115                 120                 125

Thr Val Ser Ser Ala Ser Thr Lys Gly Pro Ser Val Phe Pro Leu Ala
    130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Lys Thr Tyr Thr Cys Asn Val Asp His Lys Pro Ser Asn Thr
    210                 215                 220
```

```
Lys Val Asp Lys Arg Val Glu Ser Lys Tyr Gly Pro Pro Cys Pro Pro
225                 230                 235                 240

Cys Pro Ala Pro Glu Phe Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser Gln Glu Asp Pro Glu Val Gln Phe Asn
        275                 280                 285

Trp Tyr Val Asp Gly Val Glu Val His Asn Ala Lys Thr Lys Pro Arg
    290                 295                 300

Glu Glu Gln Phe Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Gly Leu Pro Ser Ser Ile Glu Lys Thr Ile Ser Lys Ala Lys
            340                 345                 350

Gly Gln Pro Arg Glu Pro Gln Val Tyr Thr Leu Pro Pro Ser Gln Glu
        355                 360                 365

Glu Met Thr Lys Asn Gln Val Ser Leu Thr Cys Leu Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Arg Leu Thr Val Asp Lys Ser Arg Trp Gln Glu Gly
            420                 425                 430

Asn Val Phe Ser Cys Ser Val Met His Glu Ala Leu His Asn His Tyr
        435                 440                 445

Thr Gln Lys Ser Leu Ser Leu Ser Leu Gly
    450                 455
```

<210> SEQ ID NO 54
<211> LENGTH: 458
<212> TYPE: PRT
<213> ORGANISM: Artificial Sequence
<220> FEATURE:
<223> OTHER INFORMATION: PG102_VH_2

<400> SEQUENCE: 54

```
Met Glu Trp Ser Trp Val Phe Leu Phe Phe Leu Ser Val Thr Thr Gly
1               5                   10                  15

Val His Ser Gln Val Gln Leu Gln Glu Ser Gly Pro Gly Leu Val Lys
            20                  25                  30

Pro Ser Glu Thr Leu Ser Ile Thr Cys Thr Val Ser Gly Phe Ser Leu
        35                  40                  45

Ser Arg Tyr Ser Val Tyr Trp Val Arg Gln Pro Pro Gly Lys Gly Leu
    50                  55                  60

Glu Trp Met Gly Met Met Trp Gly Gly Gly Ser Thr Asp Tyr Ser Thr
65                  70                  75                  80

Ser Leu Lys Ser Arg Leu Thr Ile Ser Lys Asp Thr Ser Lys Ser Gln
                85                  90                  95

Val Ser Leu Lys Met Ser Ser Leu Thr Ala Ala Asp Thr Ala Val Tyr
            100                 105                 110

Tyr Cys Val Arg Thr Asp Gly Asp Tyr Trp Gly Gln Gly Thr Leu Val
        115                 120                 125
```

```
Thr Val Ser Ser Ala Ser Thr Lys Gly Pro Ser Val Phe Pro Leu Ala
    130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Lys Thr Tyr Thr Cys Asn Val Asp His Lys Pro Ser Asn Thr
    210                 215                 220

Lys Val Asp Lys Arg Val Glu Ser Lys Tyr Gly Pro Pro Cys Pro Pro
225                 230                 235                 240

Cys Pro Ala Pro Glu Phe Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser Gln Glu Asp Pro Glu Val Gln Phe Asn
        275                 280                 285

Trp Tyr Val Asp Gly Val Glu Val His Asn Ala Lys Thr Lys Pro Arg
    290                 295                 300

Glu Glu Gln Phe Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Gly Leu Pro Ser Ser Ile Glu Lys Thr Ile Ser Lys Ala Lys
            340                 345                 350

Gly Gln Pro Arg Glu Pro Gln Val Tyr Thr Leu Pro Pro Ser Gln Glu
        355                 360                 365

Glu Met Thr Lys Asn Gln Val Ser Leu Thr Cys Leu Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Arg Leu Thr Val Asp Lys Ser Arg Trp Gln Glu Gly
            420                 425                 430

Asn Val Phe Ser Cys Ser Val Met His Glu Ala Leu His Asn His Tyr
        435                 440                 445

Thr Gln Lys Ser Leu Ser Leu Ser Leu Gly
    450                 455
```

<210> SEQ ID NO 55
<211> LENGTH: 458
<212> TYPE: PRT
<213> ORGANISM: Artificial Sequence
<220> FEATURE:
<223> OTHER INFORMATION: PG102_VH_3

<400> SEQUENCE: 55

```
Met Glu Trp Ser Trp Val Phe Leu Phe Phe Leu Ser Val Thr Thr Gly
1               5                   10                  15

Val His Ser Gln Val Gln Leu Gln Glu Ser Gly Pro Gly Leu Val Lys
            20                  25                  30
```

```
Pro Ser Gln Thr Leu Ser Leu Thr Cys Thr Val Ser Gly Phe Ser Leu
        35                  40                  45

Ser Arg Tyr Ser Val Tyr Trp Val Arg Gln Pro Pro Gly Lys Gly Leu
    50                  55                  60

Glu Trp Ile Gly Met Met Trp Gly Gly Gly Ser Thr Asp Tyr Asn Pro
65                  70                  75                  80

Ser Leu Lys Ser Arg Leu Thr Ile Ser Lys Asp Thr Ser Lys Ser Gln
                85                  90                  95

Val Ser Leu Lys Leu Ser Ser Leu Thr Ala Ala Asp Thr Ala Val Tyr
            100                 105                 110

Tyr Cys Val Arg Thr Asp Gly Asp Tyr Trp Gly Gln Gly Thr Leu Val
        115                 120                 125

Thr Val Ser Ser Ala Ser Thr Lys Gly Pro Ser Val Phe Pro Leu Ala
    130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Lys Thr Tyr Thr Cys Asn Val Asp His Lys Pro Ser Asn Thr
    210                 215                 220

Lys Val Asp Lys Arg Val Glu Ser Lys Tyr Gly Pro Pro Cys Pro Pro
225                 230                 235                 240

Cys Pro Ala Pro Glu Phe Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser Gln Glu Asp Pro Glu Val Gln Phe Asn
        275                 280                 285

Trp Tyr Val Asp Gly Val Glu Val His Asn Ala Lys Thr Lys Pro Arg
    290                 295                 300

Glu Glu Gln Phe Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Gly Leu Pro Ser Ser Ile Glu Lys Thr Ile Ser Lys Ala Lys
            340                 345                 350

Gly Gln Pro Arg Glu Pro Gln Val Tyr Thr Leu Pro Pro Ser Gln Glu
        355                 360                 365

Glu Met Thr Lys Asn Gln Val Ser Leu Thr Cys Leu Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Arg Leu Thr Val Asp Lys Ser Arg Trp Gln Glu Gly
            420                 425                 430

Asn Val Phe Ser Cys Ser Val Met His Glu Ala Leu His Asn His Tyr
        435                 440                 445
```

```
Thr Gln Lys Ser Leu Ser Leu Ser Leu Gly
    450                 455


<210> SEQ ID NO 56
<211> LENGTH: 458
<212> TYPE: PRT
<213> ORGANISM: Artificial Sequence
<220> FEATURE:
<223> OTHER INFORMATION: PG102_VH_4

<400> SEQUENCE: 56

Met Glu Trp Ser Trp Val Phe Leu Phe Phe Leu Ser Val Thr Thr Gly
1               5                   10                  15

Val His Ser Gln Val Gln Leu Val Glu Ser Gly Gly Gly Leu Val Lys
            20                  25                  30

Pro Gly Gly Ser Leu Arg Leu Ser Cys Ala Val Ser Gly Phe Ser Leu
        35                  40                  45

Ser Arg Tyr Ser Val Tyr Trp Ile Arg Gln Ala Pro Gly Lys Gly Leu
    50                  55                  60

Glu Trp Met Gly Met Met Trp Gly Gly Gly Ser Thr Asp Tyr Ser Thr
65                  70                  75                  80

Ser Val Lys Gly Arg Phe Thr Ile Ser Lys Asp Asn Ala Lys Thr Ser
                85                  90                  95

Val Tyr Leu Gln Met Ser Ser Leu Arg Ala Glu Asp Thr Ala Val Tyr
            100                 105                 110

Tyr Cys Val Arg Thr Asp Gly Asp Tyr Trp Gly Gln Gly Thr Leu Val
        115                 120                 125

Thr Val Ser Ser Ala Ser Thr Lys Gly Pro Ser Val Phe Pro Leu Ala
    130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Lys Thr Tyr Thr Cys Asn Val Asp His Lys Pro Ser Asn Thr
    210                 215                 220

Lys Val Asp Lys Arg Val Glu Ser Lys Tyr Gly Pro Pro Cys Pro Pro
225                 230                 235                 240

Cys Pro Ala Pro Glu Phe Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser Gln Glu Asp Pro Glu Val Gln Phe Asn
        275                 280                 285

Trp Tyr Val Asp Gly Val Glu Val His Asn Ala Lys Thr Lys Pro Arg
    290                 295                 300

Glu Glu Gln Phe Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Gly Leu Pro Ser Ser Ile Glu Lys Thr Ile Ser Lys Ala Lys
            340                 345                 350
```

```
Gly Gln Pro Arg Glu Pro Gln Val Tyr Thr Leu Pro Pro Ser Gln Glu
        355                 360                 365

Glu Met Thr Lys Asn Gln Val Ser Leu Thr Cys Leu Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Arg Leu Thr Val Asp Lys Ser Arg Trp Gln Glu Gly
            420                 425                 430

Asn Val Phe Ser Cys Ser Val Met His Glu Ala Leu His Asn His Tyr
        435                 440                 445

Thr Gln Lys Ser Leu Ser Leu Ser Leu Gly
    450                 455


<210> SEQ ID NO 57
<211> LENGTH: 458
<212> TYPE: PRT
<213> ORGANISM: Artificial Sequence
<220> FEATURE:
<223> OTHER INFORMATION: PG102_VH_5

<400> SEQUENCE: 57

Met Glu Trp Ser Trp Val Phe Leu Phe Phe Leu Ser Val Thr Thr Gly
1               5                   10                  15

Val His Ser Gln Val Gln Leu Gln Glu Ser Gly Pro Gly Leu Lys Lys
            20                  25                  30

Pro Ser Glu Thr Leu Ser Ile Thr Cys Thr Val Ser Gly Phe Ser Leu
        35                  40                  45

Ser Arg Tyr Ser Val Tyr Trp Val Lys Glu Pro Pro Gly Lys Gly Pro
    50                  55                  60

Glu Trp Met Gly Met Met Trp Gly Gly Gly Ser Thr Asp Tyr Ser Thr
65                  70                  75                  80

Ser Leu Lys Ser Lys Leu Thr Met Ser Lys Asp Thr Ser Lys Ser Gln
                85                  90                  95

Phe Ser Leu Lys Met Ser Ser Leu Thr Ala Ala Asn Thr Ala Met Tyr
            100                 105                 110

Tyr Cys Val Arg Thr Asp Gly Asp Tyr Trp Gly Gln Gly Thr Leu Leu
        115                 120                 125

Thr Val Ser Ser Ala Ser Thr Lys Gly Pro Ser Val Phe Pro Leu Ala
    130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Lys Thr Tyr Thr Cys Asn Val Asp His Lys Pro Ser Asn Thr
    210                 215                 220

Lys Val Asp Lys Arg Val Glu Ser Lys Tyr Gly Pro Pro Cys Pro Pro
225                 230                 235                 240

Cys Pro Ala Pro Glu Phe Leu Gly Gly Pro Ser Val Phe Leu Phe Pro
                245                 250                 255
```

```
Pro Lys Pro Lys Asp Thr Leu Met Ile Ser Arg Thr Pro Glu Val Thr
            260                 265                 270

Cys Val Val Val Asp Val Ser Gln Glu Asp Pro Glu Val Gln Phe Asn
        275                 280                 285

Trp Tyr Val Asp Gly Val Glu Val His Asn Ala Lys Thr Lys Pro Arg
    290                 295                 300

Glu Glu Gln Phe Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Gly Leu Pro Ser Ser Ile Glu Lys Thr Ile Ser Lys Ala Lys
            340                 345                 350

Gly Gln Pro Arg Glu Pro Gln Val Tyr Thr Leu Pro Pro Ser Gln Glu
        355                 360                 365

Glu Met Thr Lys Asn Gln Val Ser Leu Thr Cys Leu Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Arg Leu Thr Val Asp Lys Ser Arg Trp Gln Glu Gly
            420                 425                 430

Asn Val Phe Ser Cys Ser Val Met His Glu Ala Leu His Asn His Tyr
        435                 440                 445

Thr Gln Lys Ser Leu Ser Leu Ser Leu Gly
    450                 455


<210> SEQ ID NO 58
<211> LENGTH: 113
<212> TYPE: PRT
<213> ORGANISM: Artificial Sequence
<220> FEATURE:
<223> OTHER INFORMATION: Light chain variable region variant PG102_VL

<400> SEQUENCE: 58

Glu Leu Gln Leu Thr Gln Ser Pro Leu Ser Leu Pro Val Thr Leu Gly
1               5                   10                  15

Gln Pro Ala Ser Ile Ser Cys Arg Ser Ser Gln Ser Leu Ala Asn Ser
            20                  25                  30

Asn Gly Asn Thr Tyr Leu His Trp Tyr Leu Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gly Gly Thr Lys Leu Glu Ile Lys
            100                 105                 110

Arg


<210> SEQ ID NO 59
<211> LENGTH: 113
<212> TYPE: PRT
<213> ORGANISM: Artificial Sequence
<220> FEATURE:
<223> OTHER INFORMATION: Light chain variable region variant PG102_VL1
```

<400> SEQUENCE: 59

Glu Leu Gln Leu Thr Gln Ser Pro Leu Ser Leu Pro Val Thr Leu Gly
1               5                   10                  15

Gln Pro Ala Ser Ile Ser Cys Arg Ser Ser Gln Ser Leu Ala Ser Ser
            20                  25                  30

Ser Gly Asn Thr Tyr Leu His Trp Tyr Leu Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gly Gly Thr Lys Leu Glu Ile Lys
            100                 105                 110

Arg

<210> SEQ ID NO 60
<211> LENGTH: 113
<212> TYPE: PRT
<213> ORGANISM: Artificial Sequence
<220> FEATURE:
<223> OTHER INFORMATION: Light chain variable region variant PG102_VL2

<400> SEQUENCE: 60

Glu Leu Gln Leu Thr Gln Ser Pro Leu Ser Leu Pro Val Thr Leu Gly
1               5                   10                  15

Gln Pro Ala Ser Ile Ser Cys Arg Ser Ser Gln Ser Leu Ala Ser Ser
            20                  25                  30

Gln Gly Asn Thr Tyr Leu His Trp Tyr Leu Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gly Gly Thr Lys Leu Glu Ile Lys
            100                 105                 110

Arg

<210> SEQ ID NO 61
<211> LENGTH: 113
<212> TYPE: PRT
<213> ORGANISM: Artificial Sequence
<220> FEATURE:
<223> OTHER INFORMATION: Light chain variable region variant PG102_VL3

<400> SEQUENCE: 61

Glu Leu Gln Leu Thr Gln Ser Pro Leu Ser Leu Pro Val Thr Leu Gly
1               5                   10                  15

Gln Pro Ala Ser Ile Ser Cys Arg Ser Ser Gln Ser Leu Ala Asp Ser
            20                  25                  30

Gln Gly Asn Thr Tyr Leu His Trp Tyr Leu Gln Arg Pro Gly Gln Ser
        35                  40                  45

Pro Arg Leu Leu Ile Tyr Lys Val Ser Asn Arg Phe Ser Gly Val Pro

```
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gly Gly Thr Lys Leu Glu Ile Lys
            100                 105                 110

Arg


<210> SEQ ID NO 62
<211> LENGTH: 113
<212> TYPE: PRT
<213> ORGANISM: Artificial Sequence
<220> FEATURE:
<223> OTHER INFORMATION: Light chain variable region variant PG102_VL4

<400> SEQUENCE: 62

Asp Ile Val Met Thr Gln Ser Pro Leu Ser Leu Pro Val Thr Pro Gly
1               5                   10                  15

Gln Pro Ala Ser Ile Ser Cys Arg Ser Ser Gln Ser Leu Ala Ser Ser
            20                  25                  30

Gln Gly Asn Thr Tyr Leu His Trp Tyr Leu Gln Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gly Gly Thr Lys Leu Glu Ile Lys
            100                 105                 110

Arg


<210> SEQ ID NO 63
<211> LENGTH: 113
<212> TYPE: PRT
<213> ORGANISM: Artificial Sequence
<220> FEATURE:
<223> OTHER INFORMATION: Heavy chain variable region variant PG102 VH

<400> SEQUENCE: 63

Gln Val Lys Leu Gln Glu Ser Gly Pro Gly Leu Val Lys Pro Ser Glu
1               5                   10                  15

Thr Leu Ser Ile Thr Cys Thr Val Ser Gly Phe Ser Leu Ser Arg Tyr
            20                  25                  30

Ser Val Tyr Trp Ile Arg Gln Pro Pro Gly Lys Gly Pro Glu Trp Met
        35                  40                  45

Gly Met Met Trp Gly Gly Gly Ser Thr Asp Tyr Ser Thr Ser Leu Lys
    50                  55                  60

Ser Arg Leu Thr Ile Ser Lys Asp Thr Ser Lys Ser Gln Val Ser Leu
65                  70                  75                  80

Lys Met Asn Ser Leu Arg Thr Asp Asp Thr Ala Met Tyr Tyr Cys Val
                85                  90                  95

Arg Thr Asp Gly Asp Tyr Trp Gly Gln Gly Thr Thr Val Thr Val Ser
            100                 105                 110

Ser
```

<210> SEQ ID NO 64
<211> LENGTH: 113
<212> TYPE: PRT
<213> ORGANISM: Artificial Sequence
<220> FEATURE:
<223> OTHER INFORMATION: Heavy chain variable region variant PG102_VH1

<400> SEQUENCE: 64

```
Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Ser Arg Tyr
            20                  25                  30

Ser Val Tyr Trp Ile Arg Gln Pro Pro Gly Lys Gly Pro Glu Trp Met
        35                  40                  45

Gly Met Met Trp Gly Gly Gly Ser Thr Asp Tyr Ser Thr Ser Leu Lys
    50                  55                  60

Ser Arg Leu Thr Ile Ser Lys Asp Thr Ser Lys Ser Gln Val Ser Leu
65                  70                  75                  80

Lys Met Ser Ser Leu Thr Ala Ala Asp Thr Ala Val Tyr Tyr Cys Val
                85                  90                  95

Arg Thr Asp Gly Asp Tyr Trp Gly Gln Gly Thr Leu Val Thr Val Ser
            100                 105                 110

Ser
```

<210> SEQ ID NO 65
<211> LENGTH: 113
<212> TYPE: PRT
<213> ORGANISM: Artificial Sequence
<220> FEATURE:
<223> OTHER INFORMATION: Heavy chain variable region variant PG102_VH2

<400> SEQUENCE: 65

```
Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Ser Arg Tyr
            20                  25                  30

Ser Val Tyr Trp Val Arg Gln Pro Pro Gly Lys Gly Leu Glu Trp Met
        35                  40                  45

Gly Met Met Trp Gly Gly Gly Ser Thr Asp Tyr Ser Thr Ser Leu Lys
    50                  55                  60

Ser Arg Leu Thr Ile Ser Lys Asp Thr Ser Lys Ser Gln Val Ser Leu
65                  70                  75                  80

Lys Met Ser Ser Leu Thr Ala Ala Asp Thr Ala Val Tyr Tyr Cys Val
                85                  90                  95

Arg Thr Asp Gly Asp Tyr Trp Gly Gln Gly Thr Leu Val Thr Val Ser
            100                 105                 110

Ser
```

<210> SEQ ID NO 66
<211> LENGTH: 113
<212> TYPE: PRT
<213> ORGANISM: Artificial Sequence
<220> FEATURE:
<223> OTHER INFORMATION: Heavy chain variable region variant PG102_VH3

<400> SEQUENCE: 66

```
Gln Val Gln Leu Gln Glu Ser Gly Pro Gly Leu Val Lys Pro Ser Gln
1               5                   10                  15
```

-continued

```
Thr Leu Ser Leu Thr Cys Thr Val Ser Gly Phe Ser Leu Ser Arg Tyr
            20                  25                  30

Ser Val Tyr Trp Val Arg Gln Pro Pro Gly Lys Gly Leu Glu Trp Ile
        35                  40                  45

Gly Met Met Trp Gly Gly Gly Ser Thr Asp Tyr Asn Pro Ser Leu Lys
    50                  55                  60

Ser Arg Leu Thr Ile Ser Lys Asp Thr Ser Lys Ser Gln Val Ser Leu
65                  70                  75                  80

Lys Leu Ser Ser Leu Thr Ala Ala Asp Thr Ala Val Tyr Tyr Cys Val
                85                  90                  95

Arg Thr Asp Gly Asp Tyr Trp Gly Gln Gly Thr Leu Val Thr Val Ser
            100                 105                 110

Ser


<210> SEQ ID NO 67
<211> LENGTH: 113
<212> TYPE: PRT
<213> ORGANISM: Artificial Sequence
<220> FEATURE:
<223> OTHER INFORMATION: Heavy chain variable region variant PG102_VH4

<400> SEQUENCE: 67

Gln Val Gln Leu Val Glu Ser Gly Gly Gly Leu Val Lys Pro Gly Gly
1               5                   10                  15

Ser Leu Arg Leu Ser Cys Ala Val Ser Gly Phe Ser Leu Ser Arg Tyr
            20                  25                  30

Ser Val Tyr Trp Ile Arg Gln Ala Pro Gly Lys Gly Leu Glu Trp Met
        35                  40                  45

Gly Met Met Trp Gly Gly Gly Ser Thr Asp Tyr Ser Thr Ser Val Lys
    50                  55                  60

Gly Arg Phe Thr Ile Ser Lys Asp Asn Ala Lys Thr Ser Val Tyr Leu
65                  70                  75                  80

Gln Met Ser Ser Leu Arg Ala Glu Asp Thr Ala Val Tyr Tyr Cys Val
                85                  90                  95

Arg Thr Asp Gly Asp Tyr Trp Gly Gln Gly Thr Leu Val Thr Val Ser
            100                 105                 110

Ser
```

ANTAGONISTIC ANTI-HUMAN CD40 MONOCLONAL ANTIBODIES

CROSS REFERENCE

This application is a continuation of U.S. application Ser. No. 16/987,903, filed Aug. 7, 2020, which is a continuation of International Patent Application PCT/NL2019/050086, filed Feb. 11, 2019, which claims priority to EP 18156288.5, filed Feb. 12, 2018, each of which is entirely incorporated herein by reference in its entirety.

SEQUENCE LISTING

The instant application contains a Sequence Listing which has been submitted electronically in ASCII format and is hereby incorporated by reference in its entirety. Said ASCII copy, created on Oct. 20, 2021, is named 199830_729302_SL.txt and is 69,396 bytes in size.

FIELD OF THE INVENTION

The disclosure concerns antibodies that bind and antagonize CD40. These antibodies are particularly useful to inhibit immune responses and treat auto-immune diseases.

BACKGROUND OF THE INVENTION

The CD40 molecule is a type I membrane glycoprotein of 50 kDa. This protein is mainly expressed on the surface of antigen presenting cells including, B-cells, monocytes/macrophages and dendritic cell (DCs) and can also be found on a large variety of other cell types including, endothelial cells, smooth muscle cells, fibroblasts, epithelial cell and keratinocytes. The ligand for the CD40 receptor is CD40L, also called CD154. This 32 kDa protein is a type II integral membrane glycoprotein and is transiently expressed on activated $CD4^{+}$ T cells and a small population of activated $CD8^{+}$ T cells. In addition, CD40L has been found on a number of other immune cells and other cell types. CD40 and its ligand (CD40L) belong to the tumor necrosis factor (TNF) superfamily.

The interaction of CD40 with CD40L induces a variety of downstream effects. After its ligation with CD40L, CD40 is activated and enters the cell to stimulate expression of many proinflammatory and prothrombic genes. CD40-CD40L interaction is both implicated in cellular and humoral immune responses. Several studies have clearly demonstrated the involvement of CD40-CD40L interaction in various chronic inflammatory and autoimmune diseases. Therefore, interference in the CD40-CD40L interaction constitutes a potential target to modulate immune responses in order to treat immune related diseases.

Studies in murine models have shown a functional role for CD40/CD40L in various diseases. For example, CD40L transgenic mice acquire lethal inflammatory bowel disease. On the other hand, in a Severe Combined Immunodeficiency (SCID) mouse inflammatory bowel disease model it was shown that treatment with anti-CD40L antibody from the day of T-cell reconstitution completely prevented clinical and histological appearance of experimental colitis.

Patients with Crohn's disease suffer from a debilitating inflammatory disorder of the gastrointestinal tract. The disease in characterized by an influx of activated T cells, B cells and macrophages into the diseased mucosa. Mucosal immune cells are shown to play a central role in initiating an inflammatory loop in Crohn's disease. A dominant role of CD40L on the activated CD4' T cells has been suggested by previous studies on CD40/CD40L expression in Crohn's disease. The Mab 5D12 antibody was developed as a non-stimulatory antagonistic CD40 antibody. Using immunohistochemistry with the 5D12 antibody, increased levels of CD40 expression were found in diseases mucosa vs non-diseased mucosa of Crohn's disease patients. In addition, treatment of patient derived T-cells with 5D12 resulted in reduced IL-12 and TNF-α production by co-cultured monocytes. These findings implicate that the CD40 antagonistic antibody 5D12 potentially inhibits the immune response in Crohn's disease. The present disclosure provides improved antibodies for antagonizing CD40.

SUMMARY OF THE INVENTION

One aspect of the disclosure provides an anti-CD40 antibody or antigen binding fragment thereof comprising a heavy chain variable region and a light chain variable region, wherein the light chain variable region comprises, a CDR1 having the sequence RSSQSLA$Z_6$S$Z_7$GNTYLH, wherein $Z_6$ is S, and $Z_7$ is S or Q (SEQ ID NO. 1); a CDR2 having the sequence KVSNRFS (SEQ ID NO. 2); and a CDR3 having the sequence SQSTHVPWT (SEQ ID NO. 3) and wherein the heavy chain variable region comprises a CDR1 having the sequence GFS$X_{11}$SRY, wherein $X_{11}$ is I, L, or V, preferably wherein $X_{11}$ is L (SEQ ID NO. 4); a CDR2 having the sequence WGGGSTD (SEQ ID NO. 5); and a CDR3 having the sequence TDGDY (SEQ ID NO. 6).

Preferably, the anti-CD40 antibody or antigen binding fragment thereof, has a heavy chain variable region comprising the sequence: QV$X_1$L$X_2$ESG$X_3$GLVKP$X_4$ $X_5X_6$L$X_7X_9X_9$C$X_{10}$VSGFS$X_{11}$SRYSVYW$X_{12}$RQ$X_{13}$PGKG-$X_{14}$EW$X_{15}$GMMWGGGSTDY$X_{16}X_{17}$S$X_{18}$K$X_{19}$ R$X_{20}$TISKD$X_{21}X_{22}$K$X_{23}X_{24}$V$X_{25}$L$X_{26}X_{27}X_{28}$SL$X_{29}X_{30}X_{31}$DTA$X_{32}$YYCVRTDGDYWGQGT$X_{33}$VTVSS (SEQ ID NO. 7) wherein:

$X_1$ is Q; $X_2$ is Q or V: $X_3$ is P or G; $X_4$ is S or G; $X_5$ is E, Q, or G; $X_6$ is T or S; $X_7$ is S or R: $X_8$ is I or L; $X_9$ is T or S; $X_{10}$ is T or A; $X_{11}$ is I, L, or V; preferably wherein $X_{11}$ is L; $X_{12}$ is I, L, or V; preferably wherein $X_{12}$ is I or V $X_{13}$ is P or A; $X_{14}$ is P or L; $X_{15}$ is M or I; $X_{16}$ and $X_{17}$ are ST or NP; $X_{18}$ is L or V; $X_{19}$ is S or G; $X_{20}$ is L or F; $X_{21}$ is T or N; $X_{22}$ is S or A; $X_{23}$ is S or T; $X_{24}$ is Q or S; $X_{25}$ is S or Y; $X_{26}$ is K or Q; $X_{27}$ is M or L; $X_{28}$ is S; $X_{29}$ is R or T; $X_{30}$ is A; $X_{31}$ is A or E; $X_{32}$ is V and $X_{33}$ is L.

Preferably, wherein:

$X_2$ is Q; $X_3$ is P; $X_4$ is S; $X_5$ is E or Q; $X_6$ is T; $X_7$ is S; $X_9$ is T; $X_{10}$ is T; $X_{13}$ is P; $X_{18}$ is L; $X_{19}$ is S; $X_{20}$ is L; $X_{21}$ is T; $X_{22}$ is S; $X_{23}$ is S; $X_{24}$ is Q; $X_{25}$ is S; $X_{26}$ is K; $X_{29}$ is T; and $X_{31}$ is A.

Preferably, wherein:

$X_2$ is V; $X_3$ is G; $X_4$ is G; $X_5$ is G; $X_6$ is S; $X_7$ is R: $X_8$ is L; $X_9$ is S; $X_{10}$ is A; $X_{13}$ is A; $X_{14}$ is L; $X_{15}$ is M; $X_{16}$ is S; $X_{17}$ is T; $X_{19}$ is V; $X_{19}$ is G; $X_{20}$ is F; $X_{21}$ is N; $X_{22}$ is A; $X_{23}$ is T; $X_{24}$ is S; $X_{25}$ is Y; $X_{26}$ is Q; $X_{27}$ is M; $X_{29}$ is R; and $X_{31}$ is E.

Preferably, the anti-CD40 antibody or antigen binding fragment thereof, has a light chain variable region comprising the sequence:

$Z_1Z_2Z_3Z_4$TQSPLSLPVT$Z_5$GQPASISCRSSQSLA$Z_6$S$Z_7$GNTYLHWYLQ$Z_8$PGQSPRLLIYKVSNRFSGVP-DRFSGSGSGTDFTLKISRVEAEDVGVYYCSQSTHVPWTFGGGTKLEIKR (SEQ ID NO. 8); wherein:

$Z_1$ is E or D, $Z_2$ is L or I, $Z_3$ is Q or V and $Z_4$ is L or M; $Z_5$ is L or P; $Z_6$ is S or D; $Z_7$ is S or Q; and $Z_8$ is R or K.

Preferably, wherein:

$Z_1$, $Z_2$, $Z_3$ and $Z_4$ are ELQL; $Z_5$ is L; and $Z_8$ is R.

Preferably, wherein $Z_1$, $Z_2$, $Z_3$ and $Z_4$ are DIVM; $Z_5$ is P; $Z_6$ is S; $Z_7$ is Q; and $Z_8$ is K.

Preferably, the antibody or antigen binding fragment thereof is an antagonistic antihuman CD40 monoclonal antibody. Preferably the antibody or antigen binding fragment thereof, comprises a constant region of a human antibody, preferably an IgG constant region, preferably wherein said constant region is a region that is deficient in complement activation, preferably human $IgG_4$ constant region or a mutated human $IgG_1$ constant region. The disclosure further provides a nucleic acid encoding any of the antibodies or antigen binding fragments thereof disclosed herein.

The disclosure further provides a cell comprising and/or producing an antibody or antigen binding fragment thereof disclosed herein, and/or comprising a nucleic acid disclosed herein, preferably wherein the cell is a hybridoma cell, a Chinese hamster ovary cell, an NSO cell or a PER-C6™ cell. Disclosure further provides a cell culture comprising a cell disclosed herein.

One aspect of the disclosure concerns a method for producing and/or purifying any of the said antibodies or antigen binding fragments, preferably wherein the antibody is produced comprising culturing a cell as described before and harvesting said antibody from said culture.

One aspect of the disclosure provides a pharmaceutical composition comprising an antibody or antigen binding fragment thereof, nucleic acid and/or cell as disclosed. Preferably, the composition or antibody or antigen binding fragment thereof as disclosed herein are for use in the manufacture of a medicament. Preferably, the medicament is for ameliorating a symptom of autoimmune disorder, and/or an inflammatory disorder, and/or reducing graft rejection, and/or treatment of CD40 positive cancers, preferably wherein said autoimmune and/or inflammatory disorder is selected from the group of rheumatoid arthritis, systemic lupus erythematosus, multiple sclerosis, psoriasis, bullous pemphigoides and/or atopic dermatitis. Preferably, wherein said autoimmune and/or inflammatory disorder comprises inflammatory bowel disease, preferably comprises ulcerative colitis or Crohn's disease.

Amino acid sequence alignment of the variable regions of both the light chain and the heavy chain compared to the variable regions of PG102 antibody. Differences in amino acid sequence are highlighted in grey or white, depending on the extent of the alteration at the amino acid level. Identical sequences are highlighted in black. CDRs are indicated in the figure according to the Chothia's definition.

Figure 2:
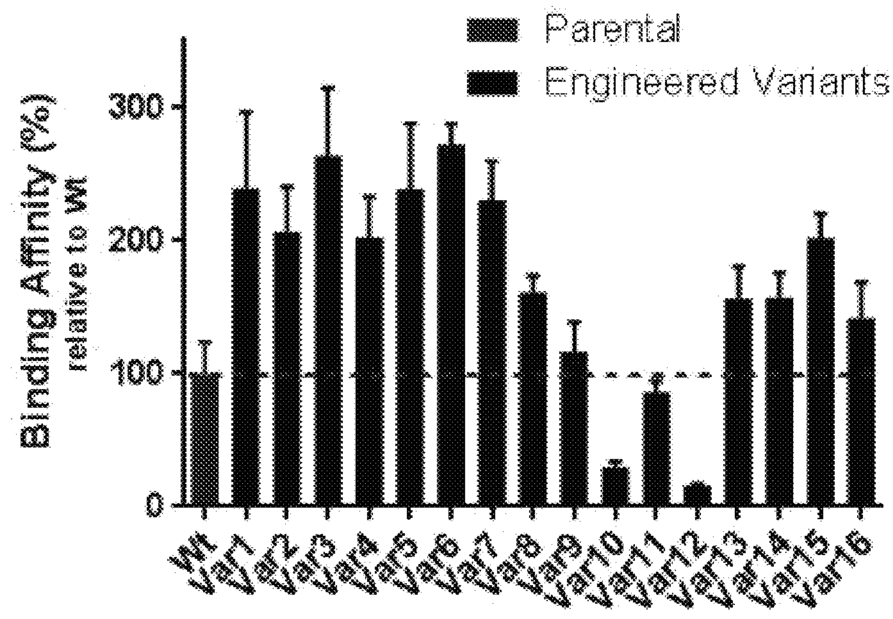
Figure 2:
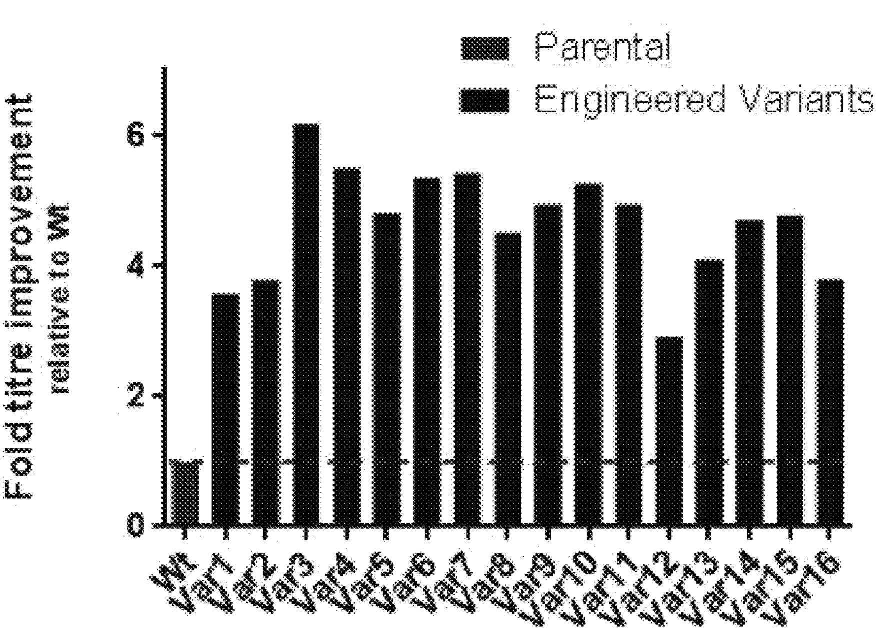

FIG. 2. Binding affinity to CD40 of PG102-variants

A. PG102 wt (parental) and engineered variants were tested for their binding affinity for CD40. Binding affinity is displayed as percentage compared to PG102 wt.

B. PG102 wt (parental) and engineered variants were tested for their fold titer improvement. Fold titer improvement is displayed as compared to PG102 that is set at 1.

Figure 3:
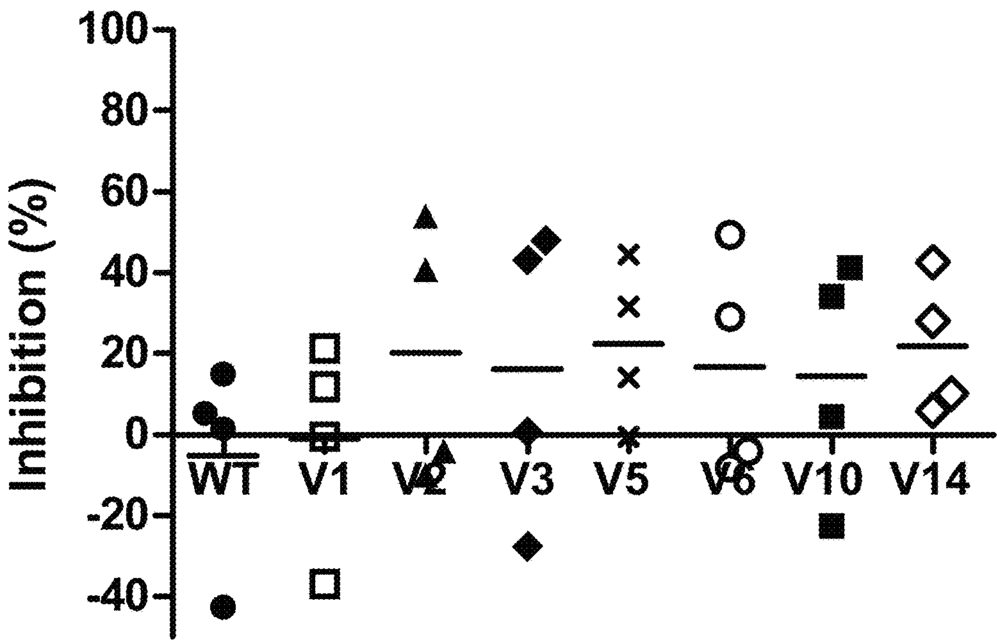
Figure 3:
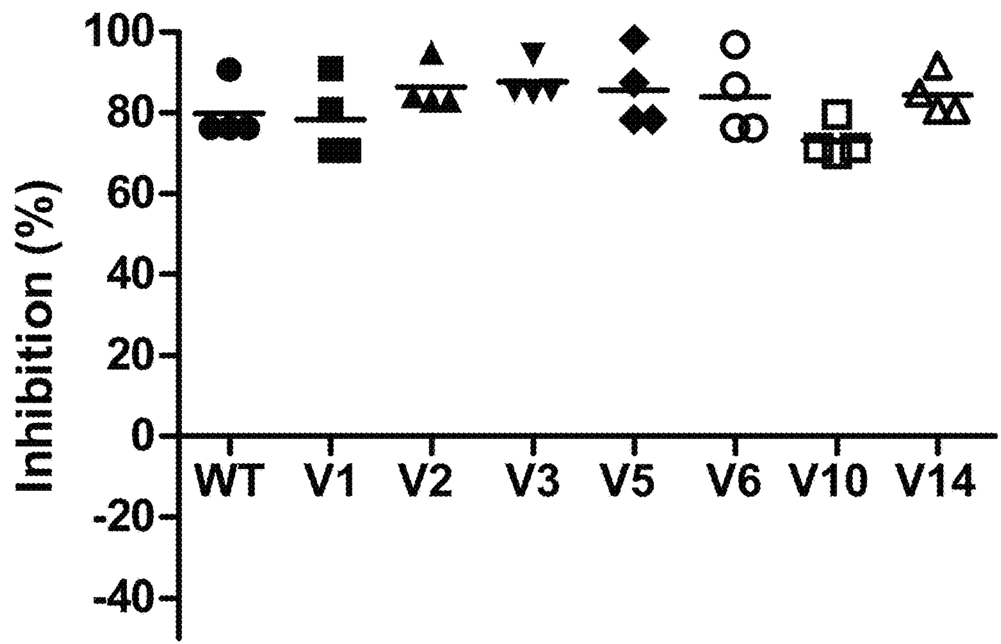

FIG. 3. TNF secretion is inhibited by treatment with monoclonal antibodies Inhibition of CD40L-induced TNF secretion by monoclonal antibodies against CD40. PG102 WT and new antibody variants are tested at a concentration of 1 ng/ml or 10 ng/ml on Peripheral blood mononuclear cells (PBMC) from four different donors (represented by data points). Graph shows percentage inhibition of TNF secretion.

Figure 4:
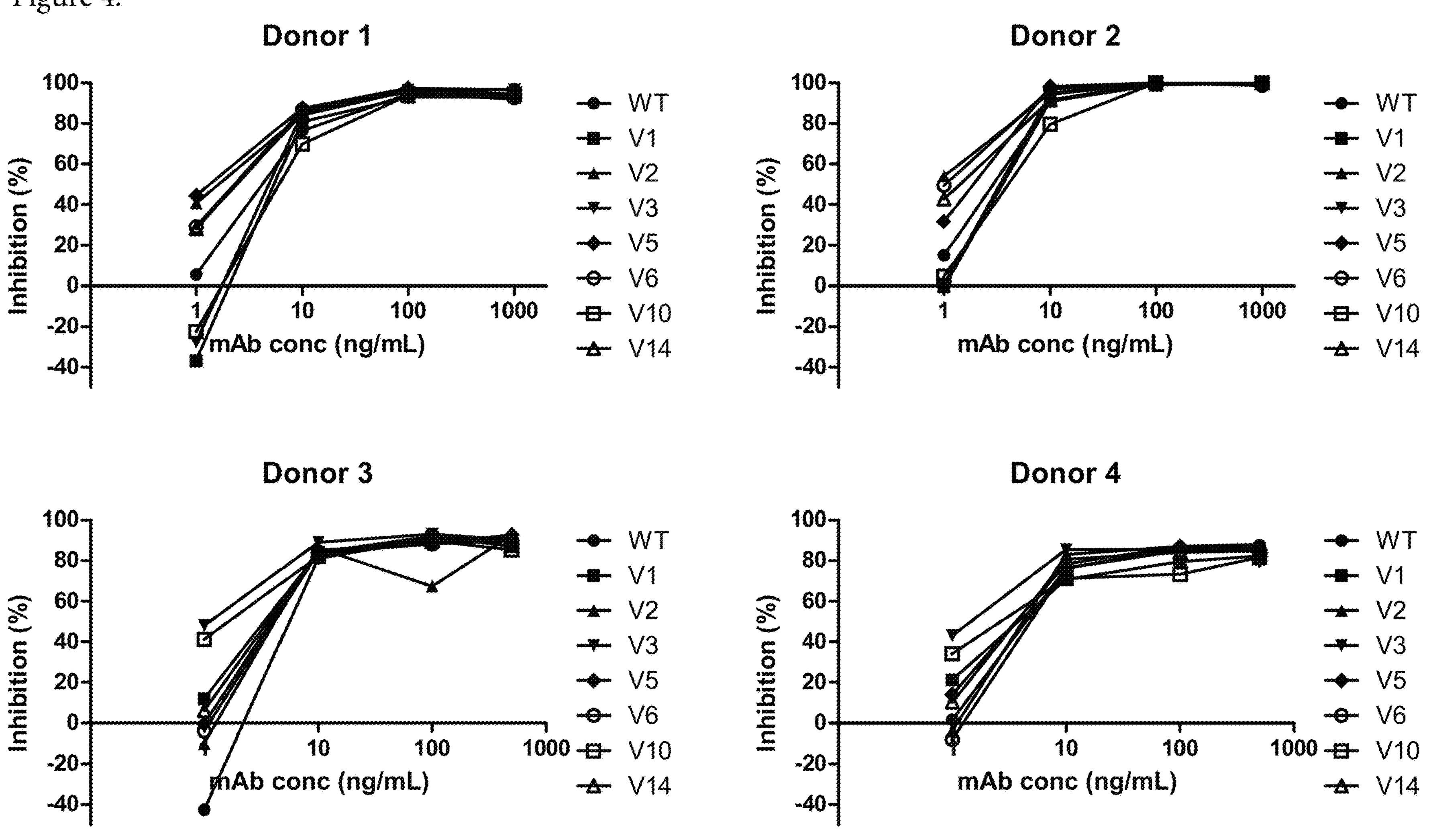

FIG. 4. TNF secretion inhibition by treatment with monoclonal anti-CD40 antibodies tested on Peripheral blood mononuclear cells (PBMC) from 4 different donors. Different antibody variants are tested on four different donors for their capacity to reduce TNF secretion after induction with CD40L the ligand of CD40. Cells are exposed to 4 different concentration ranging from 1 ng/mL to 1000 ng/mL. At the highest concentration all antibody variants show strong inhibition of the TNF secretion.

DETAILED DESCRIPTION OF THE DISCLOSED EMBODIMENTS

The disclosure concerns antibodies that bind and antagonize CD40. These antibodies are particularly useful to inhibit immune responses and treat auto-immune diseases. The Mab 5D12 antibody was developed as a non-stimulatory antagonistic CD40 antibody. WO2007/129895 describes the production of a chimeric antibody (ch5D12) having the variable heavy and light chain of Mab 5D12 with a human IgG constant domain. WO2007/129895 further describes deimmunized versions of the 5D12 antibody. One of the antibodies described in WO2007/129895 is PG102.

The present disclosure provides engineered variable regions, and antibodies and antigen binding fragments comprising said engineered variable regions, with good characteristics for the expression and manufacture of anti-CD40 antibodies. Such characteristics may include for example, protein stability, yield, CD40 binding affinity, production cell viability, and reduced immunogenicity. Such characteristics are useful when manufacturing said antibodies or antigen binding fragments thereof at a large scale. Preferably, at least one of the characteristics is improved over the PG102 antibody.

The term "antibody" as used herein refers to an immunoglobulin molecule that is typically composed of two identical pairs of polypeptide chains, each pair of chain consist of one "heavy" chain with one "light" chain. The human light chains are classified as kappa and lambda. The heavy chains comprise different classes namely: mu, delta, gamma, alpha or epsilon. These classes define the isotype of the antibody, such as IgM, IgD, IgG IgA and IgE, respectively. These classes are important for the function of the antibody and help to regulate the immune response. Both the heavy chain and the light chain consist of a variable and a constant region. The constant region of the heavy chain is clearly bigger than the constant region of the light chain, explaining the nomenclature of the heavy and light chain. Each heavy chain variable region (VH) and light chain variable region (VL) comprises complementary determining regions (CDR) interspersed by framework regions (FR). The variable region consists in total four FRs and three CDRs. These are arranged from the amino-to the carboxyl-terminus as follows: FR1. CDR1, FR2, CDR2, FR3, CDR3, FR4. The variable regions of the light and heavy chain together form the antibody binding site and defines the specificity for the epitope. The assignment of the amino acids to each region or domain of this disclosure is in accordance with the definitions of Chothia. As used herein, antigen-binding fragments include Fab, F(ab'), $F(ab')_2$, complementarity determining region (CDR) fragments, single-chain antibodies (scFv), bivalent single-chain antibodies, and other antigen recognizing immunoglobulin fragments. In some instances, the term "antibody" as used herein can be understood to also include an antigen binding fragment thereof.

One aspect of the disclosure provides an antibody and/or antigen binding fragment thereof comprising a light chain variable region. In some embodiments, the light chain variable region comprises VL-CDR1A or VL-CDR1B as CDR1, VL-CDR2 as CDR2 and VL-CDR3 as CDR3. Light chain CDRs are defined as follows:

| | | |
|---|---|---|
| VL-CDR1 | A | RSSQSLASSSGNTYLH (SEQ ID NO. 11) |
| | B | RSSQSLASSQGNTYLH (SEQ ID NO. 12) |
| VL-CDR2 | | KVSNRFS (SEQ ID NO. 13) |
| VL-CDR3 | | SQSTHVPWT (SEQ ID NO. 14) |

In both PG102 and the mouse 5D12 antibody, the CDR1 of the light chain contains three asparagine residues. Two of the asparagine residues are substituted in the light chain CDR Is described herein. While not wishing to be bound by theory, we believe that the CDR1 substitutions avoid the effects of asparagine deamidation resulting in an increase in protein yield, while still retaining CD40 binding.

In a preferred embodiment, the light chain variable region comprises VL-CDR1A as CDR1, VL-CDR2 as CDR2 and VL-CDR3 as CDR3. In another preferred embodiment, the light chain variable region comprises VL-CDR1B as CDR1, VL-CDR2 as CDR2 and VL-CDR3 as CDR3.

In some embodiments, light chain variable region comprises VL-FR1A or VL-FR1B as framework region 1, VL-FR2A or VL-FR2B as framework region 2, VL-FR3 as framework region 3, and VL-FR4 as framework region 4, as defined as follows:

| | | |
|---|---|---|
| VL-FR1 | A | ELQLTQSPLSLPVTLGQPASISC (SEQ ID NO. 15) |
| | B | DIVMTQSPLSLPVTPGQPASISC (SEQ ID NO. 16) |
| VL-FR2 | A | WYLQRPGQSPRLLIY (SEQ ID NO. 17) |
| | B | WYLQKPGQSPRLLIY (SEQ ID NO. 18) |
| VL-FR3 | | GVPDRFSGSGSGTDFTLKISRVE AEDVGVYYC (SEQ ID NO. 19) |
| VL-FR4 | | FGGGTKLEIKR (SEQ ID NO. 20) |

In a preferred embodiment, the light chain variable region comprises VL-FR1A as framework region 1, VL-FR2A as framework region 2, VL-FR3 as framework region 3, and VL-FR4 as framework region 4. In another preferred embodiment, the light chain variable region comprises VL-FR1B as framework region 1, VL-FR2B as framework region 2, VL-FR3 as framework region 3, and VL-FR4 as framework region 4.

Preferably, the light chain variable region comprises an amino acid sequence as follows: $Z_1Z_2Z_3Z_4$TQSPLS LPVT$Z_5$ GQPASISCRSSQSLA$Z_6$S$Z_7$GNTYLHWYLQ $Z_8$PGQSPRLLIYKVSNRFSGVPDRFSGSGSGTDFTLKI-SRVEAEDVGVYYCSQSTHV PWTFGGGTKLEIKR (SEQ ID NO. 8); wherein: $Z_1$, $Z_2$, $Z_3$ and $Z_4$ are ELQL or DIVM; $Z_5$ is L or P; $Z_6$ is S or D; $Z_7$ is S or Q; and $Z_8$ is R or K.

The preferred embodiments for the light chain variable region are as follows:

```
VL-1: ELQLTQSPLSLPVTLGQPASISCRSSQSLASSSGNTYLHWYLQR
      PGQSPRLLIYKVSNRFSGVPDRFSGSGSGTDFTLKISRVEAEDV
      GVYYCSQSTHVPWTFGGGTKLEIKR (SEQ ID NO. 21)
```

-continued

```
VL-2: ELQLTQSPLSLPVTLGQPASISCRSSQSLASSQGNTYLHWYLQR
      PGQSPRLLIYKVSNRFSGVPDRFSGSGSGTDFTLKISRVEAEDV
      GVYYCSQSTHVPWTFGGGTKLEIKR (SEQ ID NO. 22)

VL-4: DIVMTQSPLSLPVTPGQPASISCRSSQSLASSQGNTYLHWYLQK
      PGQSPRLLIYKVSNRFSGVPDRFSGSGSGTDFTLKISRVEAEDV
      GVYYCSQSTHVPWTFGGGTKLEIKR (SEQ ID NO. 23)
```

Figure 1:
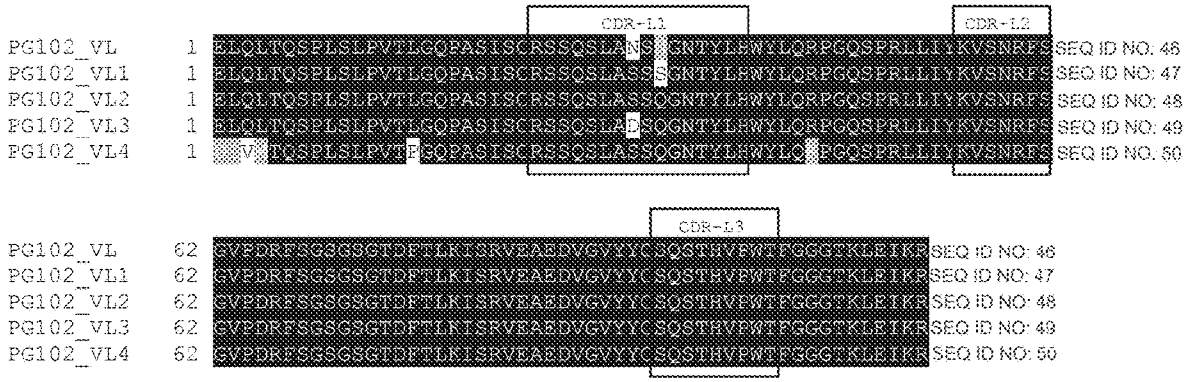
FIG. 1. Amino acid sequence alignment of variable domains
Figure 1:
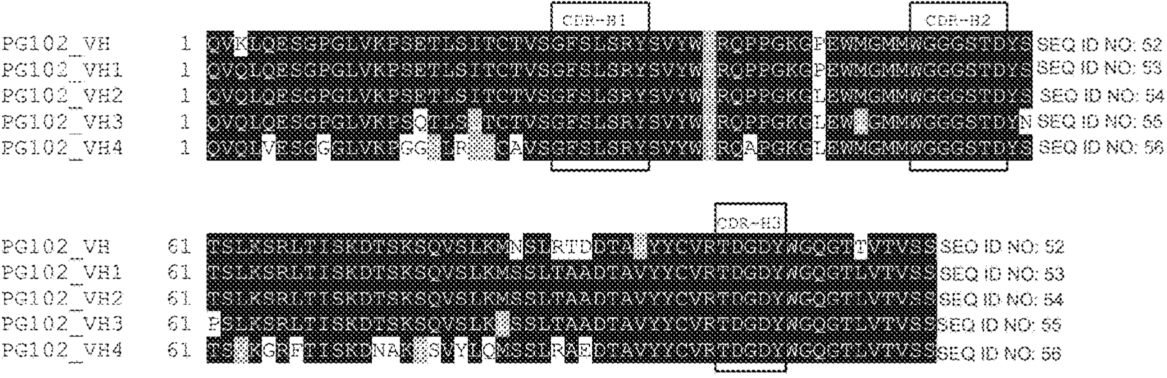

An alignment of different light chain variable regions is displayed in FIG. 1.

One aspect of the disclosure provides an antibody and/or antigen binding fragment thereof comprising a heavy chain variable region having CDRs are defined as follows:

| | | |
|---|---|---|
| VH-CDR1 | A | GFSLSRY (SEQ ID NO. 24) |
| | B | GFSISRY (SEQ ID NO. 25) |
| | C | GFSVSRY (SEQ ID NO. 26) |
| VH-CDR2 | | WGGGSTD (SEQ ID NO. 27) |
| VH-CDR3 | | TDGDY (SEQ ID NO. 28) |

As described in WO2007/129895, VH CDR1 can be VH-CDR1A, VH-CDR1B or VH-CDR1C as antibodies having these amino acid sequences all demonstrate similar CD40 binding. Preferably, VH CDR1 is VH-CDR1A or VH-CDR1C. Most preferably, VH CDR1 is VH-CDR1A.

In some embodiments, the heavy chain variable region comprises VH-FR1A, VH-FR1B or VH-FR1C as framework region 1, VH-FR2A, VH-FR2B, VH-FR2C or VH-FR2D as framework region 2, VH-FR3A, VH-FR3B or VH-FR3C as framework region 3, and VH-FR4 as framework region 4, as defined as follows:

| | | |
|---|---|---|
| VH-FR1 | A | QVQLQESGPGLVKPSETLSITCTVS (SEQ ID NO. 29) |
| | B | QVQLQESGPGLVKPSQTLSLTCTVS (SEQ ID NO. 30) |
| | C | QVQLVESGGGLVKPGGSLRLSCAVS (SEQ ID NO. 31) |
| VH-FR2 | A | SVYWIRQPPGKGPEWMGMM (SEQ ID NO. 32) |
| | B | SVYWVRQPPGKGLEWMGMM (SEQ ID NO. 33) |
| | C | SVYWVRQPPGKGLEWIGMM (SEQ ID NO. 34) |
| | D | SVYWIRQAPGKGLEWMGMM (SEQ ID NO. 35) |
| VH-FR3 | A | YSTSLKSRLTISKDTSKSQVSLKMSSLTAADTAVYYCVR (SEQ ID NO. 36) |
| | B | YNPSLKSRLTISKDTSKSQVSLKLSSLTAADTAVYYCVR (SEQ ID NO. 37) |
| | C | YSTSVKGRFTISKDNAKTSVYLQMSSLRAEDTAVYYCVR (SEQ ID NO. 38) |
| VH-FR4 | | WGQGTLVTVSS (SEQ ID NO. 39) |

In both PG102 and the mouse 5D12 antibody, FR1 contains a lysine residue at position 3. This lysine residue is substituted to a glutamine residue in all of the engineered heavy chain variants disclosed herein. While not wishing to be bound by theory, we believe that the substitution of lysine to glutamine results in a reduction of aggregation and an increase in protein expression.

In a preferred embodiment, the heavy chain variable region comprises VH-FR1A as framework region 1, VH-FR2A as framework region 2, VH-FR3A as framework region 3, and VH-FR4 as framework region 4. In another preferred embodiment, the heavy chain variable region comprises VH-FR1A as framework region 1, VH-FR2B as framework region 2, VH-FR3A as framework region 3, and VH-FR4 as framework region 4. In another preferred embodiment, the heavy chain variable region comprises VH-FR1B as framework region 1, VH-FR2C as framework region 2, VH-FR3B as framework region 3, and VH-FR4 as framework region 4. In another preferred embodiment, the heavy chain variable region comprises VH-FR1C as framework region 1, VH-FR2D as framework region 2, VH-FR3C as framework region 3, and VH-FR4 as framework region 4.

Preferably, the heavy chain variable region comprises an amino acid sequence as follows:

$QVX_{1}LX_{2}ESGX_{3}GLVKPX_{4}X_{5}X_{6}LX_{7}X_{8}X_{9}CX_{10}VSGFSX_{11}SRYSVYWX_{12}RQX_{13}PGKGX_{14}EWX_{15}GMMWGGGSTDYX_{16}X_{17}SX_{18}KX_{19}RX_{20}TISKDX_{21}X_{22}KX_{23}X_{24}VX_{25}LX_{26}X_{27}X_{28}SLX_{29}X_{30}X_{31}DTAX_{32}YYCVRTDGDYWGQGTX_{33}VTVSS$ (SEQ ID NO. 7) wherein:

$X_1$ is Q; $X_2$ is Q or V: $X_3$ is P or G; $X_4$ is S or G; $X_5$ is E, Q, or G; $X_6$ is T or S; $X_7$ is S or R: $X_8$ is I or L; $X_9$ is T or S; $X_{10}$ is T or A; $X_{11}$ is I, L, or V; preferably wherein $X_{11}$ is L; $X_{12}$ is I, L, or V; preferably wherein $X_{12}$ is I or V $X_{13}$ is P or A; $X_{14}$ is P or L; $X_{15}$ is M or I; $X_{16}$ and $X_{17}$ are ST or NP; $X_{18}$ is L or V; $X_{19}$ is S or G; $X_{20}$ is L or F; $X_{21}$ is T or N; $X_{22}$ is S or A; $X_{23}$ is S or T; $X_{24}$ is Q or S; $X_{25}$ is S or Y; $X_{26}$ is K or Q; $X_{27}$ is M or L; $X_{28}$ is S; $X_{29}$ is R or T; $X_{30}$ is A; $X_{31}$ is A or E; $X_{32}$ is V and $X_{33}$ is L.

The preferred embodiments for the heavy chain variable region are as follows:

```
VH-1:  QVQLQESGPGLVKPSETLSITCTVSGFSLSRYSVYWIRQPPGK
       GPEWMGMMWGGGSTDYSTSLKSRLTISKDTSKSQVSLKMSSLT
       AADTAVYYCVRTDGDYWGQGTLVTVSS (SEQ ID NO. 40)

VH-2:  QVQLQESGPGLVKPSETLSITCTVSGFSLSRYSVYWVRQPPGK
       GLEWMGMMWGGGSTDYSTSLKSRLTISKDTSKSQVSLKMSSLT
       AADTAVYYCVRTDGDYWGQGTLVTVSS (SEQ ID NO. 41)

VH-3:  QVQLQESGPGLVKPSQTLSLTCTVSGFSLSRYSVYWVRQPPGK
       GLEWIGMMWGGGSTDYNPSLKSRLTISKDTSKSQVSLKLSSLT
       AADTAVYYCVRTDGDYWGQGTLVTVSS (SEQ ID NO. 42)

VH-4:  QVQLVESGGGLVKPGGSLRLSCAVSGFSLSRYSVYWIRQAPGK
       GLEWMGMMWGGGSTDYSTSVKGRFTISKDNAKTSVYLQMSSLR
       AEDTAVYYCVRTDGDYWGQGTLVTVSS (SEQ ID NO. 43)
```

An alignment of different heavy chain variable regions is displayed in FIG. 1.

One aspect of the disclosure provides an antibody and/or antigen binding fragment thereof comprising a light chain variable region and heavy chain variable region as described herein.

Preferably, the antibody and/or antigen binding fragment thereof comprises a light chain comprising the CDRs of VL-1 and a heavy chain comprising the CDRs of VH-4, preferably the light chain comprises the sequence of VL-1 and the heavy chain comprises the sequence of VH4. (var4)

Preferably, the antibody and/or antigen binding fragment thereof comprises a light chain comprising the CDRs of VL-2 and a heavy chain comprising the CDRs of VH-3, preferably the light chain comprises the sequence of VL-2 and the heavy chain comprises the sequence of VH3. (var7)

Preferably, the antibody and/or antigen binding fragment thereof comprises a light chain comprising the CDRs of VL-2 and a heavy chain comprising the CDRs of VH-4, preferably the light chain comprises the sequence of VL-2 and the heavy chain comprises the sequence of VH4. (var8)

Preferably, the antibody and/or antigen binding fragment thereof comprises a light chain comprising the CDRs of VL-4 and a heavy chain comprising the CDRs of VH-1, preferably the light chain comprises the sequence of VL-4 and the heavy chain comprises the sequence of VH1. (var13)

Preferably, the antibody and/or antigen binding fragment thereof comprises a light chain comprising the CDRs of VL-4 and a heavy chain comprising the CDRs of VH-3, preferably the light chain comprises the sequence of VL-4 and the heavy chain comprises the sequence of VH3. (var15)

Preferably, the antibody and/or antigen binding fragment thereof comprises a light chain comprising the CDRs of VL-4 and a heavy chain comprising the CDRs of VH-4, preferably the light chain comprises the sequence of VL-4 and the heavy chain comprises the sequence of VH4. (var16)

More preferably, the antibody and/or antigen binding fragment thereof comprises a light chain comprising the CDRs of VL-1 and a heavy chain comprising the CDRs of VH-1, preferably the light chain comprises the sequence of VL-1 and the heavy chain comprises the sequence of VH1. (var1)

More preferably, the antibody and/or antigen binding fragment thereof comprises a light chain comprising the CDRs of VL-1 and a heavy chain comprising the CDRs of VH-2, preferably the light chain comprises the sequence of VL-1 and the heavy chain comprises the sequence of VH2. (var2)

More preferably, the antibody and/or antigen binding fragment thereof comprises a light chain comprising the CDRs of VL-1 and a heavy chain comprising the CDRs of VH-3, preferably the light chain comprises the sequence of VL-1 and the heavy chain comprises the sequence of VH3. (var3)

More preferably, the antibody and/or antigen binding fragment thereof comprises a light chain comprising the CDRs of VL-2 and a heavy chain comprising the CDRs of VH-1, preferably the light chain comprises the sequence of VL-2 and the heavy chain comprises the sequence of VH1. (var5)

More preferably, the antibody and/or antigen binding fragment thereof comprises a light chain comprising the CDRs of VL-2 and a heavy chain comprising the CDRs of VH-2, preferably the light chain comprises the sequence of VL-2 and the heavy chain comprises the sequence of VH2. (var6)

More preferably, the antibody and/or antigen binding fragment thereof comprises a light chain comprising the CDRs of VL-4 and a heavy chain comprising the CDRs of VH-2, preferably the light chain comprises the sequence of VL-4 and the heavy chain comprises the sequence of VH2. (var14)

The present disclosure provides a set of improved highly selective antibodies and antigen binding fragments thereof with antagonistic properties against CD40. These antibody variants are optimized to increase expression, while keeping or even improving their binding affinity for CD40. As exemplary embodiments, the variants referred to as Var1-8 and 13-16 all demonstrate both an increase in protein expression as well as CD40 binding affinity (see Table 2.)

Preferably, the antibodies or antigen binding fragments of the disclosure are comprised of any one of the light chain variable regions disclosed herein combined with any one of the heavy chain variable regions disclosed herein or the original PG102 heavy chain variable region; or are comprised of any one of the light chain variable regions disclosed herein or the original PG102 light chain variable region combined with any one of the heavy chain variable regions disclosed herein.

The disclosure provides variable domains having amino acid sequence which are altered at various positions compared to the PG102 antibody. The engineered variable domains, both the heavy and the light chain, are designed to improve the stability and/or expression of the antibody, while keeping and/or improving the CD40-binding properties. Increased stability is important for the production process and in vivo and in vitro stability.

An antibody according to the disclosure is preferably an antibody that is well tolerated in an animal and/or human. The engineered variable regions disclosed herein are derived from the PG102 antibody. PG102 is a deimmunized antibody having reduced immunogenicity in human as compared to the original mouse 5D12 antibody. The term "deimmunized" as used herein is defined as less immunogenic in an animal and/or human than the original antibody.

The disclosure further provides a heavy chain variable domain combined with a said light chain variable domain, as disclosed herein, in the form of a monoclonal antibody against human CD40. The antibody variable regions may be incorporated in a larger antibody molecule comprising, for example, a constant region of a human antibody. According to differences in their heavy chain constant domains, antibodies are grouped into five classes, or isotypes: IgG, IgA, IgM, IgD and IgE. These classes or isotypes comprise at least one of said heavy chains that is named with a corresponding Greek letter. In a preferred embodiment the disclosure provides an antibody according to the disclosure wherein said constant region is selected form the group of IgG, IgA, IgM, IgD and IgE constant regions, more preferably said constant region comprises an IgG constant region, more preferably an $IgG_1$ constant region, preferably a mutated $IgG_1$ constant region, most preferably said constant region is an $IgG_4$ constant region. Furthermore, said $IgG_4$ constant region is preferably a human $IgG_4$ constant region. Preferably, the $IgG_4$ constant region of the disclosure comprises the constant regions of the heavy and light chain amino acid sequence. Some variations in the constant region of $IgG_4$ occurs in nature and/or is allowed without changing the immunological properties of the resulting antibody. Typically between about 1-5 amino acid substitutions are allowed in the constant region. An antibody with an $IgG_4$ constant region or a mutated $IgG_1$ constant region has at least most of the pharmacological properties of an antibody but does not bind complement, and will thus not induce depletion of the cells its binds to in vivo. Preferably said constant region is a constant region of a human antibody.

Preferably, said constant region is a region that is deficient in complement activation, preferably a human IgG4 constant region or a mutated human $IgG_1$ constant region. CD40 binding by the antibodies and antigen binding fragments disclosed herein can be confirmed in a number of suitable assays known to the skilled person. Such assays include, e.g., affinity assays, e.g., western blots, radio-immunoassay, and ELISA (enzyme-linked immunosorbant assay). The examples describe in detail one of the many assays which can be used to measure CD40 binding.

In a further aspect, the disclosure provides nucleic acid molecules encoding said antibodies and antigen binding fragments. A nucleic acid as used in the disclosure is typically but not exclusively a ribonucleic acid (RNA) or a deoxyribonucleic acid (DNA). Based on the genetic code, a skilled person can determine the nucleic acid sequence which encode the antibody variants disclosed herein. Based on the degeneracy of the genetic code, sixty four codons may be used to encode twenty amino acids and translational terminal signal. As is known to a skilled person, codon usage bias in different organisms can effect gene expression level. Various computational tools are available to the skilled person in order to optimize codon usage depending on which organisms the desired nucleic acid will be expressed.

When said nucleic acid is expressed in a cell, the cell produces a antibody according to the disclosure. Therefore, in one embodiment a cell is provided comprising an antibody and/or a nucleic acid according to the disclosure. The host cells may be a mammalian, insect, plant, bacterial or yeast cell. Said cell is preferably a animal cell, preferably a mammalian cell, most preferably a human cell. Examples of mammalian cell lines suitable as host cells include a hybridoma cell, a Chinese hamster ovary cell, an NSO cell, or a PER-C6™ cell. For the purpose of the disclosure a suitable cell is any cell capable of comprising and preferably of producing said antibodies and/or said nucleic acids. The disclosure further encloses cell cultures that comprise said cells.

The antibodies disclosed herein can be produced by any method known to a skilled person. In a preferred embodiment, the antibodies are produced using a cell, preferably wherein the cell is a hybridoma cell, a Chinese hamster ovary cell, an NSO cell or a PER-C6™ cell. In a particular preferred embodiment said cell is a Chinese hamster ovary cell, preferably said cell is cultured in serum free medium. This includes harvesting said antibody form said culture. The antibody is preferably purified form the medium, preferably said antibody is affinity purified. Alternatively, said antibodies can be generated synthetically.

Various institutions and companies have developed cell lines for the large scale production of antibodies, for instance for clinical use. These cells are also used for other purposes such as the production of proteins. Cell lines developed for industrial scale production of proteins and antibodies are herein further referred to as industrial cell lines. Thus a preferred embodiment of the disclosure provides the use of a cell line developed for the large scale production of said antibodies.

An anti human-CD40 antibody or antigen binding fragment of the disclosure preferably comprises a heavy chain variable domain and a light chain variable domain as described herein. Such an antibody has good characteristics. It is of course possible to generate variants of such an original antibody by modifying one or more amino acids therein. Many of such variants will behave more or less similar when compared to said original. Such variants are also included in the scope of the disclosure. A non-limiting example of such a modification is an antibody comprising a pyro-glutamate instead of a glutamate. Other non-limiting examples of such modifications are an insertion, deletion, inversion and/or substitution of one or more amino acids when compared to said original antibody.

The disclosure further comprises a pharmaceutical composition comprising an antibody or antigen binding fragment as disclosed herein, or a nucleic acid encoding same, or a cell comprising an antibody or antigen binding fragment as disclosed herein, or a nucleic acid encoding same. Such compositions are especially suited for use as a medicament. The compositions may be in any suitable forms, such as liquid, semi-solid and solid dosage forms. The dosage and scheduling for the formulation, which is selected can be determined by standard procedures, well known by a skilled person. Such procedures involve extrapolating and estimating dosing schedule form animal models, and then determining the optimal dosage in a human clinical dose ranging study. The dosage in pharmaceutical compositions will vary depending upon an number of factors, such as the desired release and pharmacodynamic characteristics.

The antibodies and antigen binding fragments disclosed herein are particularly suited for ameliorating a symptom of an inflammatory disorder because of their non-stimulatory CD40 antagonizing properties. An inflammatory disorder as described herein refers to any disease that involves an inflammatory component. This specifically includes autoimmune disorders or graft rejections. The central role of CD40-CD40L interaction in the initiation, amplification and prolongation of immune responses makes said antibodies specifically suitable for immune modulation in an autoimmune disorder. Preferably the antibodies and antigen binding fragments disclosed herein are for ameliorating a symptom of an autoimmune disorder and/or anti-inflammatory disorder and/or for reducing graft rejection and/or for the treatment of CD40 positive cancers. In a preferred embodiment said autoimmune and/or an inflammatory disorder is selected form the group of inflammatory bowel disease, rheumatoid arthritis, systemic lupus erythematosus, multiple sclerosis, psoriasis, bullous pemphigoides and atopic dermatitis. Preferably wherein said autoimmune and/or inflammatory disorder comprises inflammatory bowel disease, preferably comprises ulcerative colitis or Crohn's disease.

The following information on the CD40-CD40L interaction is provided to illustrate the role of CD40 and its ligand in inflammatory disorders. The CD40 molecule is a type I membrane glycoprotein of 50 kDa. This protein is mainly expressed on the surface of antigen presenting cells including, B-cells, monocytes/macrophages and dendritic cell (DCs). Although, CD40 can also be found on a large variety of other cell types including, endothelial cells, smooth muscle cells, fibroblasts, epithelial cell and keratinocytes. The ligand for the CD40 receptor is CD40L, also called CD154. This 32 kDa protein is a type II integral membrane glycoprotein and is transiently expressed on activated $CD4^+$ T cells and a small population of activated $CD8^+$ T cells. In addition, CD40L has been found on a number of other immune cells and other cell types. CD40 and its ligand (CD40L) belong to the tumor necrosis factor (TNF) superfamily.

The interaction of CD40 with CD40L induces a variety of downstream effects. After its ligation with CD40L, CD40 is activated and enters the cell to stimulate expression of many proinflammatory and prothrombic genes. CD40-CD40L interaction is both implicated in cellular and humoral immune responses. In B cells, CD40 activation leads to a number of biological events including proliferation. Expression of activation markers, immunoglobulin production, isotype switching, homotypic adhesion and rescue form apoptosis. Activation of CD40 in monocytes/macrophages induces the secretion of large amounts of proinflammatory mediators such as IL-1, TNF-$\alpha$ and IL-12, which induce inflammatory responses and tumoricidal activity, and rescue them form apoptosis. CD40 activation also causes dendritic cells to enhance their differentiation and activation. To enhance expression of costimulatory molecules such as CD86, CD80 and CD58, to increase cytokine production, and to inhibit apoptosis. Furthermore, when expressed under inflammatory conditions. CD40 signaling can induce expression of intercellular adhesion molecules 1 (ICAM-1), vascular cell adhesion molecule 1 (VCAM-1) and E-selecting on endothelial cells. In vivo studies have indicated the importance of the CD40-CD40L interactions in the generation of humoral immune responses, in the priming and activation of antigen-specific T cells, in the temporal activation of macrophages, as well as in the protective cell-mediated immune responses through T-cell mediated macrophage activation against intracellular parasite infections such as *Pneumocystis, Cryptosporidium*, and *Leishmania.*

Several studies have clearly demonstrated the involvement of CD40-CD40L interaction in various chronic inflammatory and autoimmune diseases. Studies in murine models have shown a functional role for CD40/CD40L in various diseases. For example, CD40L transgenic mice acquire lethal inflammatory bowel disease. On the other hand, in a Severe Combined Immunodeficiency (SCID) mouse inflammatory bowel disease model it was shown that treatment with anti-CD40L from the day of T-cell reconstitution completely prevented clinical and histological appearance of experimental colitis. Evidence indicated that CD40-CD40L interactions also play a role in the pathogenesis of inflammatory bowel diseases, which includes Crohn's disease and ulcerative colitis. It was also demonstrated that interference with the CD40-CD40L pathway is strongly immunosuppressive in transplantation models. Therefore interference in the CD40-CD40L interaction constitutes a potential target to modulate immune responses in order to treat immune related diseases.

Multiple sclerosis is an autoimmune disease of the central nervous system. In this disorder, the white matter surrounding nerve fibers becomes hardened. The term multiple sclerosis literally means "many scars". Possibly the CD40-CD40L interaction is involved in the onset and/or progression of the disease, implicating that these patients might benefit from a CD40 antagonistic antibody.

Psoriasis is an inflammatory skin disease afflicting 1-2% of the population. In this disease, T cells and keratinocytes in the lesions are activated and express activation markers and co-stimulatory molecules. It is thought that some co-stimulators molecules expressed on keratinocytes and T-cells interact with each other and that these interactions contribute to disease activity. On such set of molecules may be CD40, which is expressed on activate keratinocytes, and CD40L, which is transiently expressed on activated CD4+ T-cells. Therefore, anti-CD40 antibodies may be used for the treatment of psoriasis.

Another aspect of the disclosure comprises a method for treating cancer in mammals, preferably a human, comprising administering to the mammal a therapeutically effective amount of an antibody or antigen binding fragment as described herein. In another preferred embodiment of the disclosure provides a method of preventing cancer in a mammal, preferably human, comprising administering to the mammal a therapeutically effective amount of the antibody or antigen binding fragment described herein. The term "preventing cancer" or "prevention of cancer" refers to delaying, inhibiting or preventing the onset of a cancer in a mammal, preferably human. The term also encompasses treating a mammal having premalignant conditions to stop the progression to malignancy or induce regression. Examples of premalignant conditions include hyperplasia, dysplasia and metaplasia. A further aspect of the disclosure provides a method for modulation of human CD40-mediated anti-tumor immune responses.

The antibodies may be administered alone as monotherapy, or administered in combination with one or more additional therapeutic agents or therapies. Examples of categories of additional therapeutic agents that may be used in the combination therapy to treat cancer include (1) chemotherapy agents, (2) immunotherapy agents, and (3) hormone therapeutic agents. An antibody or composition is usually administered on multiple occasions. Intervals between single doses can be, for example, weekly, monthly, every three months or yearly.

In one particular aspect, methods are provided for inhibition of immune responses in a mammal, comprising administering to the mammal a therapeutically effective amount of the antibodies and antigen binding fragments thereof disclosed herein. In some embodiments, the mammal is a human. The inhibited immune response may be cellular (i.e. cell-mediated response) or a humeral response (i.e. antibody mediated response). And maybe a primary or a secondary immune response. Examples of inhibited immune response include decreased CD4$^{+}$ helper T cell activity and reduced antibody production by B-cells. The inhibited immune response can be asses using a number of in vitro and in vivo measurement as known by the skilled person. Including but not limited to, cytotoxic T lymphocyte assays, release of cytokines, regression of tumors, survival of tumor bearing animals, antibody production, immune cell proliferation, expression of cell surface markers, and cytotoxicity.

As used herein, "to comprise" and its conjugations is used in its non-limiting sense to mean that items following the word are included, but items not specifically mentioned are not excluded. In addition the verb "to consist" may be replaced by "to consist essentially of" meaning that a compound or adjunct compound as defined herein may comprise additional component(s) than the ones specifically identified, said additional component(s) not altering the unique characteristic of the invention.

The articles "a" and "an" are used herein to refer to one or to more than one (i.e., to at least one) of the grammatical object of the article. By way of example, "an element" means one element or more than one element.

The word "approximately" or "about" when used in association with a numerical value (approximately 10, about 10) preferably means that the value may be the given value of 10 more or less 1% of the value.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

All patent and literature references cited in the present specification are hereby incorporated by reference in their entirety.

The invention is further explained in the following examples. These examples do not limit the scope of the invention, but merely serve to clarify the invention.

EXAMPLES

Example 1. In Vitro Characterization of Engineered Variants of the PG102 Antibody The wild-type recombinant PG102 antibody was expressed, along with 16 engineered variants designed to improve long-term stability, in Chinese Hamster Ovary cells (CHOK1SV GS-KO) using small scale transient expression, followed by Protein A purification and product quality analysis. Design of the variants is detailed in table 1 and the amino acid sequences are detailed in the section "appendix".

Single gene GS vectors (using Lonza's GS Xceed™ Gene Expression System) were established and progressed to transient transfections in CHOK1SV GS-KO cells to express the products. The products were purified by Protein A affinity chromatography, filter sterilized using a 0.22 µm filter cartridge, and concentrated approximately 10 fold by ultrafiltration. Product quality analysis in the form of SE-HPLC, SDS-PAGE and CD40 binding assay was carried out using purified material at 1 mg/ml.

Expression titers of variants 1 to 16 increased by approximately 3.5 to 6-fold relative to the wild-type antibody (see Table 2), whilst maintaining very low levels of aggregated material (<4%). A relative binding value could be calculated by dividing CD40 binding from the ELISA by the calculated protein concentration. Var9 to Var12 showed reduced binding affinity to CD40. The remaining antibodies maintained comparable or even improved binding affinity (see Table 2 and FIG. 2).

TABLE 1

Combinations of Heavy and Light chains used

| | | Light chains | | | | |
|---|---|---|---|---|---|---|
| Combinations | | VH | VH1 | VH2 | VH3 | VH4 |
| Heavy chains | VL | PG102 | | | | |
| | VL1 | | Var1 | Var2 | Var3 | Var4 |
| | VL2 | | Var5 | Var6 | Var7 | Var8 |
| | VL3 | | Var9 | Var10 | Var11 | Var12 |
| | VL4 | | Var13 | Var14 | Var15 | Var16 |

TABLE 2

Yield, titers and CD40 binding of PG102 variants

| a) Yield (mg/L)<br>b) Titer (mg/L)<br>c) Monomer (%)<br>d) CD 40 binding<br>e) Variant No. | VH PG102 | VH1 | VH2 | VH3 | VH4 |
|---|---|---|---|---|---|
| VLPG102 | a) 2.04<br>b) 10.20<br>c) 99.40<br>d) 14.58<br>e) PG102 | | | | |
| VL1 | | a) 7.29<br>b) 36.45<br>c) 99.46<br>d) 34.90<br>e) Var1 | a) 7.74<br>b) 38.70<br>c) 97.61<br>d) 30.08<br>e) Var2 | a) 12.58<br>b) 62.90<br>c) 99.12<br>d) 38.48<br>e) Var3 | a) 11.22<br>b) 56.10<br>c) 99.60<br>d) 29.48<br>e) Var4 |
| VL2 | | a) 9.80<br>b) 49.00<br>c) 99.28<br>d) 34.86<br>e) Var5 | a) 10.92<br>b) 54.60<br>c) 99.35<br>d) 39.67<br>e) Var6 | a) 11.07<br>b) 55.35<br>c) 99.11<br>d) 33.58<br>e) Var7 | a) 9.20<br>b) 46.00<br>c) 99.33<br>d) 23.48<br>e) Var8 |
| VL3 | | a) 10.80<br>b) 50.40<br>c) 99.31<br>d) 16.98<br>e) Var9 | a) 10.73<br>b) 53.65<br>c) 99.15<br>d) 4.35<br>e) Var10 | a) 10.08<br>b) 50.40<br>c) 98.85<br>d) 12.56<br>e) Var11 | a) 5.94<br>b) 29.70<br>c) 98.93<br>d) 2.35<br>e) Var12 |
| VL4 | | a) 8.36<br>b) 41.80<br>c) 99.16<br>d) 22.77<br>e) Var13 | a) 9.60<br>b) 48.00<br>c) 98.99<br>d) 22.96<br>e) Var14 | a) 9.75<br>b) 48.75<br>c) 99.85<br>d) 29.43<br>e) Var15 | a) 7.75<br>b) 38.75<br>c) 98.98<br>d) 20.68<br>e) Var16 |

Materials and Methods

Gene Synthesis

Heavy and light chain variable regions were synthesized by Life Technologies and subcloned into Lonza Biologics GS Xceed™ gene expression system vectors, pXC-Kappa and pXC-IgG4pro(deltaK). A 20 amino acid signal sequence was added N-terminal to the light chain sequence, and a 19 amino acid signal sequence was added N-terminal to the heavy chain Product sequences. A Kozak sequence preceded the signal sequence, following the N-terminal restriction site (section "appendix").

Single Gene Vector Construction

Single gene vectors were constructed by sub-cloning the heavy chain variable regions into the vector pXC-IgG4pro (deltaK) using the 5' restriction site HindIII and the 3' restriction site ApaI. Light chain variable regions were cloned into the vector pXC-Kappa using the 5' restriction site HindIII and the 3' restriction site BsiWI. Restriction digests were electrophoresed on 1% agarose gels and the relevant fragments gel extracted using a QIAquick gel extraction kit (QIAGEN, 28704) according to manufacturer's instructions. Ligations were set-up in a final volume of 21 μl, and incubated at room temperature for 5 min. 10 μl aliquots of the ligation reaction were used to transform One Shot Top 10 Chemically Competent *Escherichia coli* cells (Life Technologies, C404003) using the heat-shock method according to manufacturer's instructions. Cells were spread onto ampicillin-containing (50 μg/ml) Luria Bertani agar plates (LB Agar, Sigma-Aldrich L7025) and incubated overnight at 37° C. until bacterial colonies were evident. To screen for recombinants, single bacterial colonies were picked into 5 ml Luria Bertani (LB) medium (LB, Sigma-Aldrich L7275) containing 50 μg/ml ampicillin and incubated at 37° C. overnight with shaking. For heavy chain vectors DNA was isolated using the QIAGEN miniprep system (QIAprep spin miniprep kit, 27104) and eluted in 30 μl EB buffer. DNA was digested with HindIII and EcoRI to verify the presence of heavy chains insert and analyzed on an agarose gel. For light chain vectors, colonies were screened by PCR using primers binding at either end of the light chain cDNA. Positive clones for both heavy and light chain recombinants were verified by nucleotide sequencing of the gene of interest.

DNA Amplification

For Giga preps, single bacterial cultures were used to inoculate a starter culture which was subsequently used to inoculate 1.0 L LB medium containing 50 μg ampicillin and incubated at 37° C. overnight with shaking. Vector DNA was isolated using the QIAGEN Gigaprep system (Qiagen, 12291). In all instances, DNA concentration was measured using a Nanodrop 1000 spectrophotometer (Thermo-Scientific) and adjusted to 1 mg/ml. DNA quality was assessed by measuring the absorbance ratio at 260 and 280 nm.

Routine Culture of CHOK1SV GS-KO Cells

CHOK1SV GS-KO cells were cultured in CD-CHO media (Life Technologies, 10743-029) supplemented with 6 mM L-glutamine (Life Technologies, 25030-123). Cells were incubated in a shaking incubator at 36.5° C., 5% CO2, 85% humidity, 140 rpm. Cells were routinely sub-cultured every 3-4 days, seeding at 0.2×106 cells/ml and were propagated in order to have sufficient cells available for transfection. Cells were discarded by passage 20.

Transient Transfection of CHOK1SV GS-KO Cells Transient transfections were performed using CHOK1SV GS-KO cells which had been in culture a minimum two weeks. Cells were sub-cultured 24 h prior to transfection. All transfections were carried out via electroporation using the Gene Pulse XCell (Bio-Rad). For each transfection, viable cells were resuspended in pre-warmed CD-CHO media supplemented with 6 mM L-glutamine to 2.86×107 cells/ml. A combination of 40 μg of Heavy Chain SGV DNA and 40 μg of Light Chain SGV DNA was aliquoted into each cuvette (Bio-Rad, GenePulser cuvette, 0.4 cm gap, 165-2091) according to the scheme in Table 2 and 700 μl cell suspension added. Cells were electroporated at 300 V, 900 μF. Transfected cells were transferred to pre-warmed media in Erlenmeyer flasks and the contents of the cuvettes rinsed twice with pre-warmed media were also transferred to the flasks. Transfectant cultures were incubated in a shaking incubator at 36.5° C., 5% CO2, 85% humidity, 140 rpm for 6 days. Cell viability was measured at the time of harvest using a Cedex HiRes automated cell counter (Roche).

Protein A Affinity Chromatography

Culture supernatants were clarified by centrifugation followed by filtration through a 0.22 μm filter before purification by ProteinA affinity chromatography using a pre-packed 5 ml HiTrap MabSelect SuRE column (GE Healthcare, 11-0034-94) on an AKTA purifier (run at 10 ml/min). In all cases, the column was equilibrated with 50 mM sodium phosphate, 125 mM sodium chloride, pH 7.0, washed with 50 mM sodium phosphate and 1 M sodium chloride pH 7.0 followed by re-introduction of equilibration prior to elution. The molecule was eluted with 10 mM sodium formate, pH 3.5. Eluted fractions were immediately pH adjusted by neutralizing with 2×PBS buffer, pH 7.4 and titrated to approximately pH 7.2 by the addition of dilute sodium hydroxide solution.

SE-HPLC

Duplicate samples were analyzed by SE-HPLC on an Agilent 1200 series HPLC system, using a Zorbax GF-250 9.4 mm ID×25 cm column (Agilent). 80 μl aliquots of 1 mg/ml samples (or stock concentration if samples are <1 mg/ml) were injected and run in 50 mM sodium phosphate, 150 mM sodium chloride, 500 mM L-arginine, pH 6.0 at 1 ml/min for 15 minutes. Soluble aggregate levels were analyzed using Empower software. Signals arising from buffer constituents were analyzed by blank buffer injection and are omitted in the data analysis unless indicated otherwise.

SDS-PAGE Analysis

Reduced samples were prepared for analysis by mixing with NuPage 4×LDS sample buffer (Life Technologies, NP0007) and NuPage 10× sample reducing agent (Life Technologies, NP0009), and incubated at 70° C., 10 min. For non-reduced samples, the reducing agent and heat incubation were omitted. Samples were electrophoresed on 1.5 mm NuPage 4-12% Bis-Tris Novex pre-cast gels (Life Technologies, NP0316) with NuPage MES SDS running buffer under denaturing conditions. 10 μl aliquot of SeeBlue Plus 2 pre-stained molecular weight standard (Life Technologies, LC5925) and of a control antibody at 1 mg/ml were included on the gel. 1.5 μg of each sample was loaded onto the gel. Once electrophoresed, gels were stained with InstantBlue (TripleRed, ISB01L) for 30 min at room temperature. Images of the stained gels were analyzed on a BioSpectrum Imaging System (UVP).

CD40 Binding Assay

Binding of the antibody variants to CD40 was measured using an ELISA based assay based on UKSL-2057. Microtiter plates were coated with recombinant CD40 before the antibody variants were added and detected using an alkaline phosphatase conjugated antihuman kappa IgG.

Results

Vector Construction

All constructs were sub-cloned to generate single gene vectors (SGVs) as described in Section 4.2 and confirmed by EcoRI/HindIII double-digest or PCR. The final SGVs were also verified by nucleotide sequencing of the gene of interest coding regions through a third party provider.

DNA Amplification

Vector amplification was achieved following the method described in the materials and methods section. DNA quality for the double gene vectors was assessed by measuring the absorbance ratio A260/A280. This was found to be between 1.88 and 1.92.

Transient Transfections 200 ml transient transfections were established using the SGVs generated. The cultures were incubated as indicated. Cell counts upon harvest are shown in Table 3. All cultures were found to have cell growth and viability within typically observed range.

TABLE 3

Viable cell concentration and viability of small scale transfectants upon harvest

| Product | Viable Cell Concentration ($\times 10^6$ cells/ml) | Viability (%) |
|---|---|---|
| PG102_Wt | 6.73 | 90.33 |
| PG102_Var1 | 7.75 | 94.32 |
| PG102_Var2 | 7.59 | 93.64 |
| PG102_Var3 | 9.46 | 93.57 |
| PG102_Var4 | 9.21 | 93.94 |
| PG102_Var5 | 7.77 | 93.03 |
| PG102_Var6 | 6.76 | 93.04 |
| PG102_Var7 | 8.11 | 94.07 |
| PG102_Var8 | 8.03 | 94.07 |
| PG102_Var9 | 8.60 | 93.85 |
| PG102_Var10 | 8.38 | 93.93 |
| PG102_Var11 | 8.45 | 95.16 |
| PG102_Var12 | 9.52 | 95.16 |
| PG102_Var13 | 6.82 | 92.13 |
| PG102_Var14 | 6.98 | 93.38 |
| PG102_Var15 | 7.14 | 93.49 |
| PG102_Var16 | 7.04 | 94.07 |

Protein A Affinity Chromatography

Cultures were harvested on day 6 post-transfection. Supernatant was clarified by centrifugation and filtration, loaded onto a 5 ml HiTrap MabSelect SuRE column and eluted. The elution profiles for all products (FFP104_wt and FFP104_Var1 to FFP104_Var16) show a single protein species peak during the elution phase, as expected. The obtained yields for these transient cultures are summarized in Table 2.

SE-HPLC Analysis of Purified Products

Samples of purified product from the small scale evaluation transfection were analyzed by SE-HPLC on a Zorbax GF-250 9.4 mm ID×25 cm column (Agilent). A predominant (>97.6%) protein species peak was observed for all products with a retention time of approximately 8.58 min comparable to an antibody control (~8.7 min, data not shown here). The products showed an additional minor peak at shorter retention times at ~7.9 min indicating the presence of a higher molecular weight species such as soluble aggregates. SDS-PAGE Analysis of Purified Products Reduced and non-reduced samples of the purified products were electrophoresed and stained with InstantBlue. This confirmed the presence of all products and high levels of purity for PG102_Wt and PG102_Var1 to PG102_Var16. The products compare well with the control antibody: Under non-reducing conditions a protein band at >98 kDa is seen for the products comparable with the control IgG1 antibody run under the same conditions. Two bands were observed under reducing conditions consistent with the sizes of heavy (>49 kDa) and light chains (<28 kDa) and comparable with the bands found for the control antibody.

CD40 Binding Assay

The concentration of the antibody in the clarified culture supernatant was estimated from the recovered yield of the products from the Protein A affinity purification and samples were diluted to approximately 100 ng/ml in order to be within the range of the ELISA. Samples were then prepared and analyzed The results were converted to effective concentrations in the clarified supernatant to allow comparison with This assay provides an assessment of the affinity of the antibody variants for CD40. The data indicates that FFP104_Var1, FFP104_Var2, FFP104_Var5, and FFP104_Var6 show an increased level of response by CD40 ELISA than expected by Protein A derived titer suggesting comparable or improved binding affinity of these variants to CD40 (table 2 and FIG. 2). Variants FFP104_Var9 to FFP104_Var12 show a reduced response, suggesting a decrease in binding affinity to CD40.

This information suggests that variants containing the VL3 demonstrate reduced binding to CD40.

Conclusion

Small scale transient transfections of PG102_Wt along with sixteen variants were established to evaluate expression levels, Protein A purification and product quality of the variants including binding to the antigen CD40. Expression titer of the PG102_Wt was found to be 10.2 mg/L. All sixteen variants (PG102_Var1 to PG102_Var16 showed improved expression levels 3.5-6-fold higher than the PG102_Wt. These variants also showed good levels of purity by SDS-PAGE and SE-HPLC with low levels of higher molecular weight impurities such as soluble aggregates (<1.08%), comparable to the PG102_Wt parental molecule (0.6%). Results from the CD40 binding ELISA will be influenced by the affinity of the sample to CD40 as this may vary with respect to the PG102_Wt and the reference material of PG102 (lot number 364190ARS) that was used to generate the standard binding curve. A relative binding value can be determined by dividing CD40 ELISA binding data by the protein concentration as established post Protein A purification. The latter estimates the likely supernatant concentration for the expressed products as some small level of product loss (typically <10%) may be expected during the Protein A purification, eluate neutralization and buffer exchange. For the PG102_Wt antibody the correlation between ELISA and post-Protein A derived concentrations was 143%, showing fair agreement between the two assays. The data indicates that PG102_Var1, PG102_Var2, PG102_Var5, and PG102_Var6 show an increased level of response by CD40 ELISA than expected by Protein A derived titer suggesting comparable or improved binding affinity of these variants to CD40. Variants PG102_Var9 to PG102_Var12 show a reduced response, suggesting a decrease in binding affinity to CD40. This suggests that variants containing the VL3 demonstrate reduced binding to CD40.

Example 2. Testing of Biological Activity of 7 Selected PG102 Variants

A selection of seven PG102 variants was tested for its biological activity. Peripheral blood mononuclear cells (PBMC) were isolated from blood from healthy donors. TNF secretion by PBMC cells was induced using CD40L, the ligand for CD40. Seven PG102 variants are tested with PBMCs from total of four donors. Al test conditions are performed in duplo. Addition of 1, 10, 100 or 1000 ng/ml monoclonal antibody resulted in reduced levels of TNF secretion. The assay showed that five out of seven monoclonal antibodies have at least similar, or slightly increase biological activity compared to PG102_WT (table 4, FIGS. 3 and 4). This concerns the following variants: PG102_var2, PG102_var3, PG102_var5, PG102_var6 and PG102_var16. PG102_var1 and PG102_var10 show reduced biological activity at the level of 1 and 10 ng/ml and are possibly less effective than PG102_wt (table 4). For PG102_var 10, this corresponds with the CD40 binding data, showing reduced binding affinity for the antibody variants carrying the VL3 (table 2).

Materials and Methods

Measurement of CD40L-induced TNF secretion form PBMC in presence of 1, 10, 100 or 1000 ng/ml monoclonal antibody.

All Culture Conditions in Duplo

Outcome measurement: percentage inhibition of TNF secretion.

TABLE 4

Biological activity tested for seven PG102 variants

| Variant | Light chain | Heavy chain | Expression | Binding | Percentage inhibition of TNF secretion at 1 ng/ml | at 10 ng/ml |
|---|---|---|---|---|---|---|
| PG102_WT | | | 10.20 | 14.58 | −5.2 | 81.2 |
| PG102_var1 | 1 | 1 | 36.45 | 34.90 | −0.9 | 81.8 |
| PG102_var2 | 1 | 2 | 38.70 | 30.08 | 20.2 | 87.2 |
| PG102_var3 | 1 | 3 | 62.90 | 38.48 | 16.1 | 88.5 |
| PG102_var5 | 2 | 1 | 49.00 | 34.86 | 22.5 | 87.4 |
| PG102_var6 | 2 | 2 | 54.60 | 39.67 | 16.6 | 86.0 |
| PG102_var10 | 3 | 2 | 53.65 | 4.35 | 14.4 | 75.8 |
| PG102_var14 | 4 | 2 | 48.00 | 22.96 | 21.8 | 85.5 |

Example 3: In Silico Analysis of PG102 Variants

The in silico analysis is composed of a manufacturability assessment of the potential risk of aggregation and PTMs.

Materials and Methods

Antibody Engineering

The antibody engineering procedure was performed as outlined below:

1. Background information was analyzed.
2. The antibody sequences were aligned to a set of reference sequences.
3. Lonza's Antibody Aggregation platform was applied to the antibody.
4. Critical positions were identified.
5. A 3D structural model of the antibody was constructed and analyzed.
6. The sequences were screened for PTMs. Potential PTMs were categorized in terms of manufacturability risks.
7. Potential risks were analyzed and described.
8. Based on the collected data an assessment of the possibility to substitute each position was made. Positions were categorized as Neutral, Contributing or Critical.
9. A set of aggregation and PTM mitigating sequences were designed and ranked based on their potential to reduce the risk of aggregation or PTMs without negatively affecting binding affinity. Sequence and structural comparisons were made as necessary.
10. The candidate sequences were screened with Epibase™. Each remaining Th epitope or cluster of epitopes was examined and the positions therein assessed by Epibase™ for the capacity to reduce the predicted immunogenicity.
11. Deimmunizing substitutions were introduced where possible.
12. A set of recommended engineered variants was compiled.
13. An Epibase™ immunoprofiling of the engineered FFP104 variants was performed and a comparison against the Parental antibody was made.

Sequence Annotation

The updated Chothia CDR definition (Al-Lazikani et al. 1997) will be used as reference. This definition differs from the original Chothia and Lesk 1987 publication by the inclusion of the heavy chain Chothia positions H:57 and H:58 in the CDR H2 definition. Positional numbering is ordinal unless otherwise specified, in which case Chothia numbering (Chothia and Lesk 1987) will be used.

Sequence Alignments

Multiple alignments of the Parental sequence to the mouse and human germline sequences were generated and entries in each alignment were ordered according to the sequence identity (SeqID) to the Parental sequence. Reference sets were reduced to a unique set of sequences by clustering at 100% SeqID and excluding redundant entries.

Antibody Aggregation

The antibody aggregation platform used in this study was developed using a machine learning algorithm based on sequence and structural features of antibodies (Obrezanova et al. 2015). The predictive aggregation model was trained and tested on a set of antibodies, designed to cover a wide chemical space and to contain low and high expressing as well as aggregating and non-aggregating antibodies. The characteristics of all antibodies in the set were experimentally determined in-house. The algorithm gives a categorical output of high or low risk of aggregation; antibodies in the higher category have an increased risk of aggregation above 5% after one-step Protein A purification. In addition to the high or low aggregation risk categorization the antibody aggregation platform generates a certainty score which can be used to compare the aggregation propensity of related antibodies.

Identification of Residues at Critical Positions

Antibody variable domains (Fv) have a number of critical positions that make up the VH/VL inter chain interface or are responsible for the discrete set of canonical structures that has been defined for 5 of the CDRs (Chothia and Lesk 1987, Al Lazikani et al. 1997); these positions should be considered in detail before substitutions are proposed for them. Table 5 and Table 6 below show the conserved positions within the VH/VL interface and the positions that determine the CDR canonical class (respectively), with numbering according to the Chothia definition.

TABLE 5

Conserved positions within the VH/VL interface

| Domain | Positions |
|---|---|
| VL | 34, 36, 38, 43, 44, 46, 87, 88, 89, 91, 96, 98 |
| VH | 35, 37, 39, 45, 47, 91, 93, 95, 100-100K*, 101, 103 |

All positions are according to Chothia numbering

*The numbering of the positions one N-terminal to position 101 differs by CR H3 length

TABLE 6

| Positions determining CDR canonical class | |
|---|---|
| CDR | Key residues |
| L1 | 2, 25, 29, 30, 30D*, 33, 71 |
| L2 | 34 |
| L3 | 90, 94, 95, 97 |
| H1 | 24, 26, 29, 34, 94 |
| H2 | 54, 55, 71 |

All positions are according to Chothia numbering
*If CDR L1 is long enough to contain the position Construction of 3D Models Structural models of the Fv-region for antibody PG102, and variants thereof, were generated using Lonza's modelling platform. Candidate structural template fragments for the framework (FR) and CDRs as well as the full Fv were scored, ranked and selected from an in-house antibody database based on their sequence identity to the target, as well as qualitative crystallographic measures of the template structure, such as the resolution (in Ångstrom (Å)).

In order to structurally align the CDRs to the FR templates, 5 residues on either side of the CDR were included in the CDR template. An alignment of the fragments was generated based on overlapping segments and a structural sequence alignment generated. The template fragments along with the alignment were processed by MODELLER (Sali et al. 1993). This protocol creates conformational restraints derived from the set of aligned structural templates. An ensemble of structures that satisfy the restraints is created by conjugate gradient and simulated annealing optimization procedures. One or more model structures are selected from this ensemble on the basis of an energy score, derived from the score of the protein structure and satisfaction of the conformational restraints. The models were inspected and the side chains of the positions which differ between the target and template were optimized using a side chain optimization algorithm and energy minimized. A suite of visualization and computational tools were used to assess the conformational variability of the CDRs, as well as the core and local packing of the domains and regions and a surface analysis to select one or more preferred models.

Comparison of Modelled Structures

Structural models for the Parental and engineered Fv-regions are modelled individually, as described above (4.6), to ensure the variant models are not constructed with any inherent bias towards the Parental model structure. However, the high sequence identity of the engineered variants to the Parental sequence often results in identical structural templates being selected for many models.

To assess the impact of different substitutions on affinity and stability, a number of structural criteria are used. The solvent accessibility, local atomic packing and location of the substitution relative to the predicted antigen binding interface or the Fv dimer interface are key criteria. The observation of an unfavorable solvation state, bad inter-atomic contacts or the poor placement of an inappropriate residue at a key position leads to the rejection of a potential substitution. Other criteria, such as electrostatic effects, hydrogen bonding patterns or potential hydrogen bonding patterns are also used to assess the suitability of a substitution. Some positions are more suitable than others for the acceptance of substitutions as a set of critical positions play a role in supporting the canonical class of CDRs, the packing of the individual domain cores or the inter-domain interfaces.

Post-Translational Modifications

PTMs can cause problems during the development of a therapeutic protein such as increased heterogeneity, reduced bioactivity, reduced stability, immunogenicity, fragmentation and aggregation. The potential impact of PTMs depends on their location and in some cases on solvent exposure. The sequences were analyzed for the following potential PTMs: Asparagine deamidation, Aspartate isomerization, free Cysteine thiol groups, N- and O-glycosylation, N-terminal cyclization, oxidation and pyroglutamate formation. The three types of PTM determined to be relevant for the two antibodies in this study are described in more detail below.

Asparagine Deamidation

The hydrolysis of the amide group on the side-chain of Asparagine, deamidation, is a nonenzymatic reaction that over time produces a heterogeneous mixture of Asparagine, isoAspartate and Aspartate at the effected position. In addition to causing charge heterogeneity, Asparagine deamidation can affect protein function if it occurs in a binding interface such as in antibody CDRs (Harris et al. 2001). The deamidation rate is influenced by pH and local conformation, in particular the succeeding residue of the Asparagine (Robinson and Robinson 2004).

Aspartate Isomerization

Aspartate isomerization is the non-enzymatic interconversion of Aspartate and isoAspartate amino acid residues. As well as causing charge heterogeneity, Asparagine deamidation can affect protein function if it occurs in a binding interface such as in antibody CDRs (Harris et al. 2001). The isomerization reaction proceeds through intermediates similar to those of the Asparagine deamidation reaction and the risk can normally be minimized by careful tuning of process parameters and formulation.

Oxidation

Methionine and to a lesser extent Tryptophan are susceptible to non-site specific oxidation. While Methionine is primarily sensitive to free reactive oxygen species, Tryptophan is more sensitive to light induced oxidation. The degree of sensitivity is largely determined by the solvent accessibility of the side-chain; buried residues are less sensitive or take longer to react. Oxidative damage can be caused during production, purification, formulation or storage and can affect stability and biological activity.

Assessment of Potential Substitutions

All positions in the variable domain of the antibody were assessed for their potential impact on binding affinity and stability. Each position was classified as either: Neutral, Critical or Contributing.

Neutral—a substitution to another amino acid at this position should not affect binding affinity or stability.

Contributing—a substitution can be made but the position may be contributing to the binding affinity or stability. Retention of the Parental amino acid at this position should be considered.

Critical—the position must retain the Parental amino acid or risk a decreased binding affinity or reduced stability.

There are many factors that contribute to this categorization, originating from concerns over both affinity and stability. The factors contributing to the classification are:

- Positions responsible for antigen binding
- Critical positions
  - Conserved residues within the VH/VL interface
  - Positions determining CDR canonical class
- Distance from the CDRs
- Conservation or variation at the position in the reference alignment
- Solvent accessibility Local atomic packing
Local secondary structure
Electrostatic effects
Hydrogen bonding patterns
Hydrogen bonding potential
Post-translational modifications Critical positions are initially defined as those in the Chothia CDRs, determined to be at critical positions in the VH/VL interface (fable 5); at positions that help determine the CDR conformation (Table 6) or that are highly conserved in the reference alignment.

Neutral substitutions are generally solvent exposed positions in the framework and more than 5 Å from any side chain atoms of any CDR residues. Residues within this region are classed as Contributing to the affinity. Contributing positions may be substituted, and in many cases this is done in order to efficiently humanize, deimmunize or otherwise engineer an antibody. The risk category of all positions is continually re-evaluated in the context of other substitutions.

Many positions are conserved and will only accept a small set, or only one, type of amino acid. Other positions are more variable and if they are found to be solvent exposed and remote to the CDRs then they can support almost any substitution.

Analysis of Epitopes

Epitopes, or clusters of adjoining epitopes, were analyzed using Epibase™ for substitutions that would remove or reduce binding to HLA allotypes to the greatest extent possible, with a focus on the HLA-DRB1 allotypes. Substitutions at Neutral positions were preferred over Contributing positions and substitutions at Critical positions could only be proposed after a visual inspection and reclassification of the position as Contributing. Substitutions were selected to be as conservative as possible. Human germline sequences were not considered to be immunogenic as they are found in the pool of circulating antibodies. Substitutions that would introduce new epitopes or binding to additional allotypes for existing epitopes were identified and removed from consideration.

Combinations of substitutions are sometimes required to remove epitopes, especially when there is a cluster of epitopes or promiscuous epitopes. As with single substitutions, combinations have to be monitored so that they do not introduce binding to additional HLA allotypes.

Immunoprofile Comparison

Epibase™ immunoprofile of the engineered antibody variants against the 85 HLA class II allotypes in the Global set was performed in the same manner as for the Parental sequence.

A comparison of antibody variants with respect to their immunogenic risk using only HLA binding predictions is very difficult. This is because several important factors are not considered:

The binding peptide may not be generated by the processing machinery and therefore it would never be exposed as a peptide-HLA complex to Th cells by antigen presenting cells.

The peptide-HLA complex may not be recognized by a Th cell.

Given these considerations, three types of quantitative comparisons can be made using Epibase™ Immunoprofiling between variant sequences. Firstly, the number of critical epitopes for each of the DRB1, DRB3/4/5, DQ and DP allotype sets can be compared, with peptides binding to multiple allotypes of the same group counted as one. Such an epitope count shows the number of unique epitopes within each set and the difference between the Parental and engineered protein reveals the complete removal of potential Th epitopes.

However, many epitopes, especially promiscuous epitopes binding multiple allotypes, are difficult to completely remove. Consequently, the change in the unique Th epitope count may obscure the actual reduction of the immunogenicity potential. Therefore the second quantitative comparison is at the level of each HLA allotype over all Th epitopes, where a count of the binding peptides per allotype for the Parental and engineered variants, taken together with the serotype and population frequency allows a comparison at either the serotype or allotype level. (See Results). Thirdly, an approximate score expressing a worst-case immunogenic risk can be calculated as follows:

$$\text{score}=\Sigma(\text{Epitope Count}\times\text{Allotype Frequency})$$

The multiplicative product for each affected allotype is calculated from the number of epitopes predicted to bind a given allotype, and the allele frequency of the affected allotype. The products are summed for all DRB1 allotypes used in the study. It should be noted that the score is not the absolute metric by which to measure immunogenicity risk, and that the substitutions proposed, and their order, take all chosen HLA allotypes (DRB1, DRB3/4/5, DQ and DP) into account as well as the substitution position and category.

Further characterization of PG102 demonstrated that there are three regions detected in mass spectroscopy following Trypsin digestion where the tryptic peptides had a deamidation above comparably low levels (<4%). One is a known deamidation site in the conserved domains, two are in the variable domain: tryptic peptides H10 (MNSLR) in the VH and tryptic peptide L2 (SSQSLANSNGNTYLHWYLQRPGQSPR) in the VL.

The L2 tryptic peptide is in the CDR L1 region of the light chain and potentially affects binding efficiency for the molecule. Light chain CDR L1 contains three potential deamidation motifs, two of which were experimentally verified (L:Asn31 and L:Asn33). However, the stability study indicates that deamidation in CDR L1 has a comparatively small impact on antigen binding. After 12 months at +25° C. and with 100% deamidation the product specific antigen binding ELISA is at 95% activity compared to reference.

Low levels of Methionine oxidized variants were detected for three tryptic peptides in mass spectroscopy results. Two VH sites were affected, H:Met82 and H:Met92, with the report noting that the tryptic peptide H1, containing H:Met92, may be more susceptible to Methionine oxidation when the PG102 drug product is stored at +25° C. The initial analysis highlighted the Methionine's in CDR H2 of the heavy chain as a potential cause of the aggregation issue. The stability study results shows that the Methionine's H:Met48, H:Met50 and H:Met51 are all buried within the antibody and not accessible.

Epibase™ Immunoprofiling

Epibase™ immunoprofiling against the 85 HLA class II allotypes in the Global set was performed on the sequences of the parental antibody and the engineered variant PG102_var16.

Post-Translational Modifications

Post-translational modifications (PTMs) can cause problems during the development of a therapeutic protein such as increased heterogeneity and in some instances reduced bioactivity or reduced stability. PTMs located in the CDRs are of particular concern for antibodies as the modification can alter the bioactivity. There are several potential PTMs, described in Table 7, that pose a potential manufacturability risk.

TABLE 7

| Potential post-translations; modifications of note | | | |
|---|---|---|---|
| Chain | Region | Amino acid position | Description |
| L | L1 | L: Asn31 | CDR L1 Asparagine with deamidation potential. Experimentally verified. |
| L | L1 | L: Asn33 | CDR L1 Asparagine with deamidation potential. Experimentally verified. |
| L | L1 | L: Asn35 | CDR L1 Asparagine with deamidation potential. PTM at this position has the potential to affect binding. The site is buried and therefore less likely to degrade. No specific mention of deamidation of this site in report R02990. Monitoring for the presence of the PTM and process control are the suggested mitigation strategies. |
| L | L3 | L: Trp101 | CDR L3 Tryptophan with oxidation potential. Not experimentally detected. PTM at this position has the potential to affect binding. Monitoring for the presence of the PTM and process control are the suggested mitigation strategies. |
| H | FR1 | H: Gln1 | N-terminal Glutamine with high potential to form pyroglutamate. Pyroglutamate formation from N-terminal Glutamine is common in antibodies. Pyroglutamate formation experimentally verified in report R02990. Low risk. |
| H | H2 | H: Met50 | Buried CDR H2 Methionine with low oxidation risk. Not experimentally detected. PTM at this position has the potential to affect binding. Low risk. |
| H | H2 | H: Met51 | Buried CDR H2 Methionine with low oxidation risk. Not experimentally detected. PTM at this position has the potential to affect binding. Low risk. |
| H | H2 | H: Trp52 | CDR H2 Tryptophan with oxidation potential. Not experimentally detected. PTM at this position has the potential to affect binding. Monitoring for the presence of the PTM and process control are the suggested mitigation strategies. |
| H | FR3 | H: Asn83 | Asparagine with deamidation potential. Experimentally verified |
| H | FR3 | H: Met92 | Methionine with oxidation potential. Experimentally verified. |
| H | H3 | H: Asp99 | CDR H3 Aspartic acid with isomerisation potential. Not experimentally detected. PTM at this position has the potential to affect binding. Low risk. |

Potential engineered variant sequences were screened using Lonza's Antibody Aggregation platform and Epibase™.

Each position was screened with all possible amino acid substitutions using Lonza's Antibody Aggregation platform and the results recorded. The assessment of each position was updated as work progressed to reflect the positions impact on aggregation, PTMs and immunogenicity based on the screening tool as well as sequence and structural analysis.

It was found that subsequent to the PTM engineering of the light chains there were few avenues to improve the antibody by decreasing the aggregation propensity risk by substitutions in the light chain. Therefore, the engineered light chain focusses on the CDR L1 PTMs and has a single engineered chain with additional substitutions. There was more scope to improve the antibody by decreasing the predicted aggregation propensity risk in the heavy chain. An increasing number of de-aggregating framework substitutions has been proposed in three heavy engineered chains. Moreover, it was found that the aggregation risk could be further decreased by using a germline from another human VH family as reference, in this case VH3-3-11. This option has been explored in one engineered heavy chain, FFP_VH_4.

The final proposed substitutions and their effects are described below for the light and heavy chains. Eight substitutions have been proposed for the light chain and thirty for the heavy chain, with a large number stemming from the approach taken for the last engineered heavy chain FFP104_VH_4. The engineered chains are shown in FIG. 1 for light and heavy chain respectively. The amino acid sequences of all engineered chains are available in in the "detailed description of the disclosed embodiments". An alignment of the engineered sequences to the Parental can be found in FIG. 1.

Each candidate sequence was analyzed for substitutions that modify the predicted immunogenicity, and those that increased it were avoided. The present study has focused on the 43 DRB1 allotypes available in Epibase™, as DRB1 allotypes are the most relevant for immunogenicity assessments.

Antibody Aggregation Results

The Antibody Aggregation prediction results for Parental PG102 and the engineered variants are given in Table 8. The platform predicts whether the antibody is in a Low or High Aggregation Risk Class. The aggregation score is related to the class with positive scores indicating a High Risk Class and negative scores the Low Risk Class. The absolute value of the Aggregation Score indicates an increased certainty in the prediction. Hence, a more negative Aggregation Score is sought in this project. The ΔScore indicates the change from the Parental antibody, with a more negative score being preferable.

The Parental antibody PG102 was already predicted to be in the Low Risk class but with a comparatively high score, i.e. close to zero. One engineered heavy chain PG102_VH_2, has resulted in an increased Aggregation Score for four variants. As noted above, this chain was designed in order to evaluate a minimal number of framework substitutions.

TABLE 8

| Antibody aggregation results | | | |
|---|---|---|---|
| Variant Name | Risk Class | Aggregation Score | ΔScore |
| PG102 | Low | −0.6 | |
| PG102_var1 | Low | −0.2 | 0.6 |
| PG102_var2 | Low | −0.8 | −0.2 |
| PG102_var3 | Low | −1.2 | −0.6 |
| PG102_var4 | Low | −1.3 | −0.8 |
| PG102_var5 | Low | −0.2 | 0.4 |
| PG102_var6 | Low | −0.8 | −0.2 |
| PG102_var7 | Low | −1.2 | −0.6 |
| PG102_var8 | Low | −1.3 | −0.8 |
| PG102_var9 | Low | −0.2 | 0.4 |
| PG102_var10 | Low | −0.8 | −0.2 |
| PG102_var11 | Low | −1.2 | −0.6 |
| PG102_var12 | Low | −1.3 | −0.8 |
| PG102_var13 | Low | −0.2 | 0.4 |
| PG102_var14 | Low | −0.8 | −0.2 |
| PG102_var15 | Low | −1.2 | −0.6 |
| PG102_var16 | Low | −1.3 | −0.8 |

ΔScore = Parental PG 102 Score − variant score

Epibase™ Immunoprofiling Comparison

The engineered variant combination of PG102 (PG102_var16) was taken through Epibase™ immunoprofiling. As the level of detail in the Epibase™ profiles is too granular to compare in detail, a comparison based on three types of immunoprofile statistics was performed between the Parental antibody and the engineered variants. The overall predicted immunogenicity risk potential is lower in the engineered variants; however it is still comparable to that of the parental PG102.

Example 4

The disclosure further provides alterations in the light chain variable domain (FIG. 1). In the light chain two Asparagine (N) amino acids at position 31 and 33 in the variable domain are replaced by Serine (S), Glutamine (Q) or Aspartic acid (D) (FIG. 1). These alterations are believed to prevent Asparagine deamidation. The hydrolysis of the amide group in the side-chain of Asparagine, deamidation, is a non-enzymatic reaction that over time produces a heterogeneous mixture of Asparagine, isoAspartate and Aspartate at the effected position. In addition to causing charge heterogeneity, Asparagine deamidation can affect protein function if it occurs in a binding interface such as the antibody CDR. Both Asparagine residues were located in the CDR1 of the light chain and are replaced to prevent deamidation.

The disclosure further provides alterations designed in the heavy chain variable region (FIG. 1). The third amino acid position of the heavy chain variable region is altered from lysine (K) to Glutamine (Q) for all new antibody variants. This alteration improves the stability of the antibody and reduces the aggregational properties during purification and storage. Framework region 3 of the PG102 antibody comprised the sequence MNSLR, including as Asparagine (N) amino acid. This amino acid is replaced by Serine (S) to prevent deamidation of the antibody. Amino acids RTD at the positions 86, 87 and 88 in the heavy chain variable region are substituted to Threonine (T), Alanine (A) or Glutamine (Q) in order to reduce aggregation. The Methionine residue at position 92 in the heavy chain variable region is replaced by Valine (V) to prevent methionine oxidation.

APPENDIX

Amino Acid Sequences

Light chain sequences

PG102_VL (SEQ ID NO. 46)
MSVPTQVLGLLLLWLTDARCELQLTQSPLSLPVTLGQPASISCRSSQSLANSNGNTYLHWYLQRPGQSPRLL
IYKVSNRFSGVPDRFSGSGSGTDFTLKISRVEAEDVGVYYCSQSTHVPWTFGGGTKLEIKRTVAAPSVFIFP
PSDEQLKSGTASWCLLNNFYPREAKVQWKVDNALQSGNSQESVTEQDSKDSTYSLSSTLTLSKADYEKHKVY
ACEVTHQGLSSPVTKSFNRGEC

PG102_VL_1 (SEQ ID NO. 47)
MSVPTQVLGLLLLWLTDARCELQLTQSPLSLPVTLGQPASISCRSSQSLASSSGNTYLHWYLQRPGQSPRLL
IYKVSNRFSGVPDRFSGSGSGTDFTLKISRVEAEDVGVYYCSQSTHVPWTFGGGTKLEIKRTVAAPSVFIFP
PSDEQLKSGTASWCLLNNFYPREAKVQWKVDNALQSGNSQESVTEQDSKDSTYSLSSTLTLSKADYEKHKVY
ACEVTHQGLSSPVTKSFNRGEC

PG102_VL_2 (SEQ ID NO. 48)
MSVPTQVLGLLLLWLTDARCELQLTQSPLSLPVTLGQPASISCRSSQSLASSQGNTYLHWYLQRPGQSPRLL
IYKVSNRFSGVPDRFSGSGSGTDFTLKISRVEAEDVGVYYCSQSTHVPWTFGGGTKLEIKRTVAAPSVFIFP
PSDEQLKSGTASVVCLLNNFYPREAKVQWKVDNALQSGNSQESVTEQDSKDSTYSLSSTLTLSKADYEKHKV
YACEVTHQGLSSPVTKSFNRGEC

PG102_VL_3 (SEQ ID NO. 49)
MSVPTQVLGLLLLWLTDARCELQLTQSPLSLPVTLGQPASISCRSSQSLADSQGNTYLHWYLQRPGQSPRLL
IYKVSNRFSGVPDRFSGSGSGTDFTLKISRVEAEDVGVYYCSQSTHVPWTFGGGTKLEIKRTVAAPSVFIFP
PSDEQLKSGTASWCLLNNFYPREAKVQWKVDNALQSGNSQESVTEQDSKDSTYSLSSTLTLSKADYEKHKVY
ACEVTHQGLSSPVTKSFNRGEC

PG102_VL_4 (SEQ ID NO. 50)
MSVPTQVLGLLLLWLTDARCDIVMTQSPLSLPVTPGQPASISCRSSQSLASSQGNTYLHWYLQKPGQSPRLL
IYKVSNRFSGVPDRFSGSGSGTDFTLKISRVEAEDVGVYYCSQSTHVPWTFGGGTKLEIKRTVAAPSVFIFP
PSDEQLKSGTASVVCLLNNFYPREAKVQWKVDNALQSGNSQESVTEQDSKDSTYSLSSTLTLSKADYEKHKV
YACEVTHQGLSSPVTKSFNRGEC

PG102_VL_5 (SEQ ID NO. 51)
MSVPTQVLGLLLLWLTDARCDIVMTQSPLSLPYTPGQPASISCRSSQSLAASAGATYLHWYLEKPGGPPRRL
IYKVSNRFSGVPDRFSGSGSGTDFTLKISRVEAEDVGVYYCSQSTHVPWTFGGGTKLEIKRTVAAPSVFIFP
PSDEQLKSGTASWCLLNNFYPREAKVQWKVDNALQSGNSQESVTEQDSKDSTYSLSSTLTLSKADYEKHKVY
ACEVTHQGLSSPVTKSFNRGEC

Heavy chain sequences

PG102_VH (SEQ ID NO. 52)
MEWSWVFLFFLSVTTGVHSQVKLQESGPGLVKPSETLSITCTVSGFSLSRYSVYWIRQPPGKGPEWMGMMWG
GGSTDYSTSLKSRLTISKDTSKSGVSLKMNSLRTDDTAMYYCVRTDGDYWGQGTTVTVSSASTKGPSVFPLA
PCSRSTSESTAALGCLVKDYFPEPVTVSWNSGALTSGVHTFPAVLQSSGLYSLSSVVTVPSSSLGTKTYTCN
VDHKPSNTKVDKRVESKYGPPCPPCPAPEFLGGPSVFLFPPKPKDTLMISRTPEVTCVVVDVSQEDPEVQFN
WYVDGVEVHNAKTKPREEQFNSTYRVVSVLTVLHQDWLNGKEYKCKVSNKGLPSSIEKTISKAKGQPREPQV
YTLPPSQEEMTKNQVSLTCLVKGFYPSDIAVEWESNGQPENNYKTTPPVLDSDGSFFLYSRLTVDKSRWQEG
NVFSCSVMHEALHNHYTQKSLSLSLG

APPENDIX-continued

Amino Acid Sequences

PG102_VH_1 (SEQ ID NO. 53)
MEWSWVFLFFLSVTTGVHSQVQLQESGPGLVKPSETLSITCTVSGFSLSRYSVYWIRQPPGKGPEWMGMMWG
GGSTDYSTSLKSRLTISKDTSKSQVSLKMSSLTAADTAVYYCVRTDGDYWGQGTLVTVSSASTKGPSVFPLA
PCSRSTSESTAALGCLVKDYFPEPVTVSWNSGALTSGVHTFPAVLQSSGLYSLSSVVTVPSSSLGTKTYTCN
VDHKPSNTKVDKRVESKYGPPCPPCPAPEFLGGPSVFLFPPKPKDTLMISRTPEVTCVVVDVSQEDPEVQFN
WYVDGVEVHNAKTKPREEQFNSTYRVVSVLTVLHQDWLNGKEYKCKVSNKGLPSSIEKTISKAKGQPREPQV
YTLPPSQEEMTKNQVSLTCLVKGFYPSDIAVEWESNGQPENNYKTTPPVLDSDGSFFLYSRLTVDKSRWQEG
NVFSCSVMHEALHNHYTQKSLSLSLG

PG102_VH_2 (SEQ ID NO. 54)
MEWSWVFLFFLSVTTGVHSQVQLQESGPGLVKPSETLSITCTVSGFSLSRYSVYWVRQPPGKGLEWMGMMWG
GGSTDYSTSLKSRLTISKDTSKSOVSLKMSSLTAADTAVYYCVRTDGDYWGQGTLVTVSSASTKGPSVFPLA
PCSRSTSESTAALGCLVKDYFPEPVTVSWNSGALTSGVHTFPAVLQSSGLYSLSSVVTVPSSSLGTKTYTCN
VDHKPSNTKVDKRVESKYGPPCPPCPAPEFLGGPSVFLFPPKPKDTLMISRTPEVTCVWDVSQEDPEVQFNW
YVDGVEVHNAKTKPREEQFNSTYRWSVLTVLHQDWLNGKEYKCKVSNKGLPSSIEKTISKAKGQPREPQVYT
LPPSQEEMTKNQVSLTCLVKGFYPSDIAVEWESNGQPENNYKTTPPVLDSDGSFFLYSRLTVDKSRWQEGNV
FSCSVMHEALHNHYTQKSLSLSLG

PG102_VH_3 (SEQ ID NO. 55)
MEWSWVFLFFLSVTTGVHSQVQLQESGPGLVKPSQTLSLTCTVSGFSLSRYSVYWVRQPPGKGLEWIGMMWG
GGSTDYNPSLKSRLTISKDTSKSQVSLKLSSLTAADTAVYYCVRTDGDYWGQGTLVTVSSASTKGPSVFPLA
PCSRSTSESTAALGCLVKDYFPEPVTVSWNSGALTSGVHTFPAVLQSSGLYSLSSVVTVPSSSLGTKTYTCN
VDHKPSNTKVDKRVESKYGPPCPPCPAPEFLGGPSVFLFPPKPKDTLMISRTPEVTCVVVDVSQEDPEVQFN
WYVDGVEVHNAKTKPREEQFNSTYRVVSVLTVLHQDWLNGKEYKCKVSNKGLPSSIEKTISKAKGQPREPQV
YTLPPSQEEMTKNQVSLTCLVKGFYPSDIAVEWESNGQPENNYKTTPPVLDSDGSFFLYSRLTVDKSRWQEG
NVFSCSVMHEALHNHYTQKSLSLSLG

PG102_VH_4 (SEQ ID NO. 56)
MEWSWVFLFFLSVTTGVHSQVQLVESGGGLVKPGGSLRLSCAVSGFSLSRYSVYWIRQAPGKGLEWMGMMWG
GGSTDYSTSVKGRFTISKDNAKTSVYLQMSSLRAEDTAVYYCVRTDGDYWGQGTLVTVSSASTKGPSVFPLA
PCSRSTSESTAALGCLVKDYFPEPVTVSWNSGALTSGVHTFPAVLQSSGLYSLSSVVTVPSSSLGTKTYTCN
VDHKPSNTKVDKRVESKYGPPCPPCPAPEFLGGPSVFLFPPKPKDTLMISRTPEVTCVVVDVSQEDPEVQFN
WYVDGVEVHNAKTKPREEQFNSTYRVVSVLTVLHQDWLNGKEYKCKVSNKGLPSSIEKTISKAKGQPREPQV
YTLPPSQEEMTKNQVSLTCLVKGFYPSDIAVEWESNGQPENNYKTTPPVLDSDGSFFLYSRLTVDKSRWQEG
NVFSCSVMHEALHNHYTQKSLSLSLG

PG102_VH_5 (SEQ ID NO. 57)
MEWSWVFLFFLSVTTGVHSQVQLQESGPGLKKPSETLSITCTVSGFSLSRYSVYWVKEPPGKGPEWMGMMWG
GGSTDYSTSLKSKLTMSKDTSKSQFSLKMSSLTAANTAMYYCVRTDGDYWGQGTLLTVSSASTKGPSVFPLA
PCSRSTSESTAALGCLVKDYFPEPVTVSWNSGALTSGVHTFPAVLQSSGLYSLSSVVTVPSSSLGTKTYTCN
VDHKPSNTKVDKRVESKYGPPCPPCPAPEFLGGPSVFLFPPKPKDTLMISRTPEVTCVVVDVSQEDPEVQFN
WYVDGVEVHNAKTKPREEQFNSTYRVVSVLTVLHQDWLNGKEYKCKVSNKGLPSSIEKTISKAKGQPREPQV
YTLPPSQEEMTKNQVSLTCLVKGFYPSDIAVEWESNGQPENNYKTTPPVLDSDGSFFLYSRLTVDKSRWQEG
NVFSCSVMHEALHNHYTQKSLSLSLG

Variable regions are underlined and flanked by the secretion signal sequences (N-terminal) and constant regions (C-terminal).

The invention claimed is:

1. An anti-CD40 antibody or antigen binding fragment thereof, comprising:

a heavy chain variable region, wherein the heavy chain variable region comprises:

(i) a CDR1 that comprises the sequence set forth in SEQ ID NO: 4 or a variant thereof, wherein the variant consists of a modification of a leucine (L) at position 4 to an isoleucine (I) or a valine (V) as compared to the sequence of SEQ ID NO: 4;

(ii) a CDR2 that comprises the sequence set forth in SEQ ID NO: 5;

(iii) a CDR3 that comprises the sequence set forth in SEQ ID NO: 6;

a light chain variable region, wherein the light chain variable region comprises:

(iv) a CDR1 that comprises the sequence set forth in SEQ ID NO: 1 or a variant thereof, wherein the variant consists of a modification of a serine(S) at position 8 to an aspartate (D) as compared to the sequence of SEQ ID NO: 1;

(v) a CDR2 that comprises the sequence set forth in SEQ ID NO: 2; and (vi) a CDR3 that comprises the sequence set forth in SEQ ID NO: 3.

2. The anti-CD40 antibody or antigen binding fragment thereof of claim 1, wherein the light chain variable region comprises the sequence set forth in SEQ ID NO: 1.

3. The anti-CD40 antibody or antigen binding fragment thereof of claim 1, wherein the light chain variable region comprises a variant of the sequence set forth in SEQ ID NO: 1, and wherein the variant consists of a modification of a serine(S) at position 8 to an aspartate (D) as compared to SEQ ID NO: 1.

4. The anti-CD40 antibody or antigen binding fragment thereof of claim 1, wherein the light chain variable region comprises a variant of the sequence, and wherein Xaa at position 10 of SEQ ID NO: 1 is serine(S) a serine(S) as compared to SEQ ID NO: 1.

5. The anti-CD40 antibody or antigen binding fragment thereof of claim 1, wherein the light chain variable region comprises a variant of the sequence set forth in SEQ ID NO: 1, and wherein Xaa at position 10 of SEQ ID NO: 1 is glutamine (Q).

6. The anti-CD40 antibody or antigen binding fragment thereof of claim 1, wherein the light chain variable region comprises the sequence set forth in SEQ ID NO: 21, SEQ ID NO: 22, or SEQ ID NO: 23.

7. The anti-CD40 antibody or antigen binding fragment thereof of claim 1, wherein the heavy chain variable region comprises a variant of SEQ ID NO: 4, and wherein the variant consists of a modification of a leucine (L) at position 4 to an isoleucine (I).

8. The anti-CD40 antibody or antigen binding fragment thereof of claim 1, wherein the heavy chain variable region comprises a variant of SEQ ID NO: 4, and wherein the variant consists of a modification of a leucine (L) at position 4 to a valine (V).

9. The anti-CD40 antibody or antigen binding fragment thereof of claim 1, wherein the anti-CD40 antibody or antigen binding fragment thereof comprises a human IgG constant region that is deficient in complement activation.

10. The anti-CD40 antibody or antigen binding fragment thereof of claim 1, comprising a light chain comprising a sequence set forth in any one of SEQ ID NOS: 22, 47-50; and a heavy chain comprising a sequence set forth in any one of SEQ ID NOS: 41, 53-56.

11. A pharmaceutical composition comprising the anti-CD40 antibody or antigen binding fragment thereof of claim 1.

* * * * *